United States Patent [19]

Matsumoto et al.

[11] Patent Number: 4,931,371

[45] Date of Patent: Jun. 5, 1990

[54] ELECTROPHOTOGRAPHIC PHOTOSENSITIVE MEMBER

[75] Inventors: Masakazu Matsumoto; Shozo Ishikawa, both of Yokohama; Wataru Ando, Ibaraki; Toshihiro Kikuchi, Yokohama; Itaru Yamazaki, Tokyo, all of Japan

[73] Assignee: Canon Kabushiki Kaisha, Tokyo, Japan

[21] Appl. No.: 274,503

[22] Filed: Nov. 21, 1988

[30] Foreign Application Priority Data

Nov. 24, 1987 [JP] Japan ................... 62-296443
Nov. 24, 1987 [JP] Japan ................... 62-296444
Nov. 24, 1987 [JP] Japan ................... 62-296446
Nov. 24, 1987 [JP] Japan ................... 62-296447
Nov. 26, 1987 [JP] Japan ................... 62-299045

[51] Int. Cl.$^5$ .......................... G03G 5/14; G03G 5/06
[52] U.S. Cl. ......................................... 430/59; 430/56; 430/58; 430/66
[58] Field of Search .................... 430/56, 58, 59, 66

[56] References Cited

U.S. PATENT DOCUMENTS

| 3,837,851 | 9/1974 | Shattuck et al. | 430/59 |
| 3,871,882 | 3/1975 | Weidemann | 430/58 |
| 4,150,987 | 4/1979 | Anderson et al. | 430/59 |
| 4,529,678 | 7/1985 | Ohta | 430/59 X |

FOREIGN PATENT DOCUMENTS

| 51-94828 | 8/1976 | Japan . | |
| 51-94829 | 8/1976 | Japan . | |
| 53-26128 | 3/1978 | Japan . | |
| 59-182456 | 10/1984 | Japan | 430/59 |
| 60-19150 | 1/1985 | Japan | 430/59 |
| 60-164745 | 8/1985 | Japan . | |
| 62-134652 | 12/1985 | Japan . | |
| 62-39863 | 2/1987 | Japan . | |
| 63-30853 | 2/1988 | Japan | 430/58 |

Primary Examiner—Roland E. Martin
Attorney, Agent, or Firm—Fitzpatrick, Cella, Harper & Scinto

[57] ABSTRACT

An electrophotographic photosensitive member comprises a photosensitive layer on a conductive support, wherein said photosensitive layer contains a compound, having structures (A) and (B) together in its structural formula and wherein said photosensitive layer contains a thioether compound represented by Formula (VI).

17 Claims, 1 Drawing Sheet

ELECTROPHOTOGRAPHIC PHOTOSENSITIVE MEMBER

BACKGROUND OF THE INVENTION

1. Field of the Invention

The present invention relates to an electrophotographic photosensitive member, and more particularly to an electrophotographic photosensitive member comprising a low-molecular organic photoconductive material that can impart improved electrophotographic characteristics.

2. Related Background Art

Various types of organic photoconductive polymers including polyvinyl carbazole have been hitherto proposed as photoconductive materials used in electrophotographic photosensitive members. These polymers, however, have been put into practical use with difficulty up to the present, notwithstanding their superiority to inorganic photoconductive materials in respect of film-forming properties and lightness in weight. This is because they have achieved no sufficient film-forming properties and also are inferior to the inorganic photoconductive materials in respect of sensitivity, durability, and stability against environmental changes. Also proposed are low-molecular organic photoconductive materials such as hydrazone compounds as disclosed in U.S. Pat. No. 4,150,987, triarylpyrazoline compounds as disclosed in U.S. Pat. No. 3,837,851, and 9-styryl anthracene compounds as disclosed in Japanese Patent Laid-Open Application No. 51-94828 and Japanese Patent Laid-Open Application No. 51-94829. Such low-molecular organic photoconductive materials have become able to eliminate the disadvantage in film-forming properties that has been questioned in the field of organic photoconductive polymers, by appropriately selecting binders to be used. They, however, can not be said to be sufficient in respect of the sensitivity.

Under such circumstances, a laminated structure comprising a photosensitive layer separated into a charge generation layer and a charge transport layer has been proposed in recent years. Electrophotographic photosensitive members having the photosensitive layer of this laminated structure have become able to improve the sensitivity, charge retension, surface strength, etc. to visible light. Such electrophotographic photosensitive members are disclosed, for example, in U.S. Pat. Nos. 3,837,851 and No. 3,871,882.

However, in the electrophotographic photosensitive members employing the conventional low-molecular molecular organic photoconductive material in the charge transport layer, although the sensitivity and properties thereof have reached a practical level, no sufficient solution has been achieved for the disadvantage that light portion potential and dark portion potential may greatly fluctuate when charging and exposure to light are repeatedly carried out. To suppress this fluctuation of potential during repeated use, Japanese Patent Laid-Open Application No. 57-122444 and No. 62-39863, for example, disclose a method in which an antioxidant is mixed into the charge transport layer, and besides, Japanese Patent Laid-Open Applications Nos. 53-26128, No. 60-164745, No. 62-105151, etc. teach a method in which a stabilizer is added to effect stabilization. These methods, however, are presently under the conditions that no sufficient effect can be achieved particularly when the photosensitive members are repeatedly used over a long period of time.

SUMMARY OF THE INVENTION

An object of the present invention is to provide an electrophotographic photosensitive member that can suffer less potential fluctuation even when the charge and exposure to light are repeated over a long period of time.

Another object of the present invention is to provide an electrophotographic photosensitive member that has a high sensitivity.

A further object of the present invention is to provide an electrophotographic photosensitive member that can prevent a blank area development caused by ozone, $NO_x$ or the like.

Still another object of the present invention is to provide an electrophotographic photosensitive member having an excellent durability.

Namely, the present invention provides an electrophotographic photosensitive member having a photosensitive layer on a conductive support, wherein said photosensitive layer contains the following compound, said compound having structures (A) and (B) together in its structural formula.

(A) A disubstituted aminoraryl group represented by Formula (I):

Formula (I)

wherein $R_1$ and $R_2$ each represent an alkyl group, aryl group or aralkyl group that may have a substituent, or a residual group necessary to form a ring of 5 or 6 members by the combination of R1 with R2, and Ar1 represents an arylene group that may have a substituent.

(B) A (di)sulfide structure selected from the group consisting of (1) to (4):

(1) A chain sulfide structure represented by Formula (II):

Formula (II)

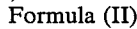

wherein $R_3$ represents an alkyl group or aralkyl group that may have a substituent.

(2) A chain disulfide structure represented by Formula (III):

Formula (III)

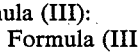

wherein $R_4$ represents an alkyl group, aryl group or aralkyl group that may have a substituent.

(3) A chain sulfide structure represented by Formula (IV) and a chain sulfide structure represented by Formula (V):

Formula (IV)

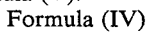

wherein $R_5$ represents an aryl group that may have a substituent.

Formula (V)

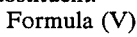

wherein $R_6$ represents an alkyl group, aryl group or aralkyl group that may have a substituent.

(4) A cyclic sulfide structure or cyclic disulfide structure containing two or more sulfur atoms.

The present invention also provides an electrophotographic photosensitive member having a photosensitive layer on a conductive support, wherein said photosensitive layer contains a thioether compound represented by Formula (VI):

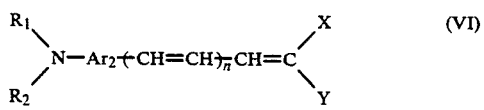

wherein $R_1$ and $R_2$ each represent an alkyl group, aralkyl group or aryl group that may have a substituent, or a residual group necessary to form a ring or 5 or 6 members by the combination of $R_1$ with $R_2$; $Ar_2$ represents an arylene group or divalent heterocyclic group that may have a substituent; n represents an integer of 0 or 1; X represents $S-R_7$ or

and Y represents $S-R_9$, an alkyl group, aralkyl group or aryl group that may have a substituent, or X and Y represent a residual group necessary to form a thioether ring by the combination of X with Y. $R_7$, $R_8$ and $R_9$ each represent an alkyl group, aralkyl group or aryl group that may have a substituent.

DETAILED DESCRIPTION OF THE INVENTION

Figure 1A:
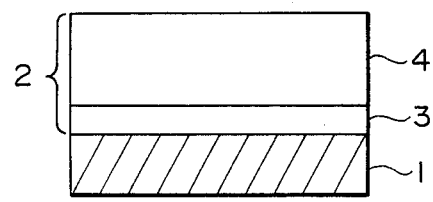
FIGS. 1A and 1B illustrate a layer constitution of the electrophotographic photosensitive member according to the present invention.

In the compound of the present invention, contained in the photosensitive layer, $R_1$ and $R_2$ of the structure designated by (A), i.e., the disubstituted aminoaryl group represented by Formula (I), each specifically represent an alkyl group such as methyl, ethyl, propyl and butyl, an aryl group such as phenyl, naphthyl, anthryl or biphenyl, an aralkyl group such as benzyl, phenethyl or naphthylmethyl, or a residual group necessary to form a cyclic amino group of 5 or 6 members such as pyrrolidino, piperidino or morpholino by the combination of $R_1$ with $R_2$.

$Ar_1$ represents an arylene group such as phenylene, naphthylene, biphenylene or anthrylene.

On the other hand, in the structures designated by (B), $R_3$ of the sulfide structure designated by (1), i.e., the chain sulfide structure represented by Formula (II), specifically represents an alkyl group such as methyl, ethyl, propyl or butyl, or an aralkyl group such as benzyl, phenethyl or naphthylmethyl.

Also, the groups represented by $R_1$, $R_2$, $Ar_1$ and $R_3$ each may have a substituent, and the substituent for these includes an alkyl group such as methyl, ethyl or butyl, an alkoxy group such as methoxy, ethoxy or propoxy, an aralkyl group such as benzyl, phenethyl or naphtylmethyl, a halogen atom such as fluorine, chlorine, bromine or iodine, a hydroxyl group, or a mercapto group.

The compound according to the present invention, having together the disubstituted aminoaryl group represented by Formula (I) and the chain sulfide structure represented by Formula (II), is constituted by combining the above disubstituted aminoaryl group with the chain sulfide structure moiety, but there are no particular limitations on the means for combining them. More specifically, the two structural moieties may be directly combined, or may be combined through a conjugated or non-conjugated organic group, or further may be combined in the form in which aryl moieties or the like are covalently bonded, thereby exhibiting an excellent effect. In short, is satisfactory if the disubstituted aminoaryl group and the chain sulfide structure moiety coexist in the same molecule.

The reason why this structure can bring about a specifically good effect against the deterioration of performance owing to repeated use is not clear, but it is presumed that the basicity of N of the disubstituted aminoaryl group and the d-orbital effect attributable to the sulfur atom in sulfide cooperatively act on the environmental deterioration factors such as ozone, $NO_x$ and nitric acid, generated inside a copying machine, to prevent penetration of the environmental deterioration factors.

Among these compounds, the compound represented by the following general formula (VII) is especially preferable.

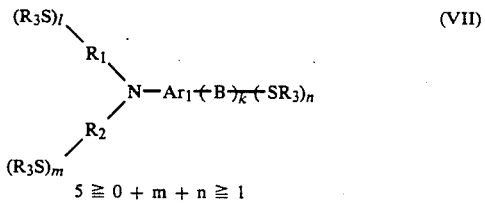

(wherein Q and m are an integer of 0 or 1; n an integer of 0, 1, 2 or 3; k an integer of 0 or 1; B represents a di- or tri-valent hydrocarbon group, a di- or tri-valent hydrocarbon group having one or two of a nitrogen atom or a tri-valent nitrogen atom group, and specifically, includes

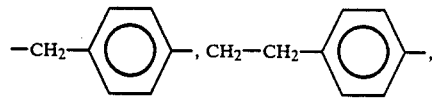

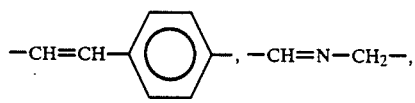

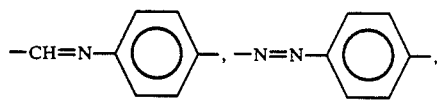

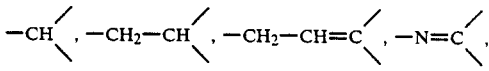

-continued

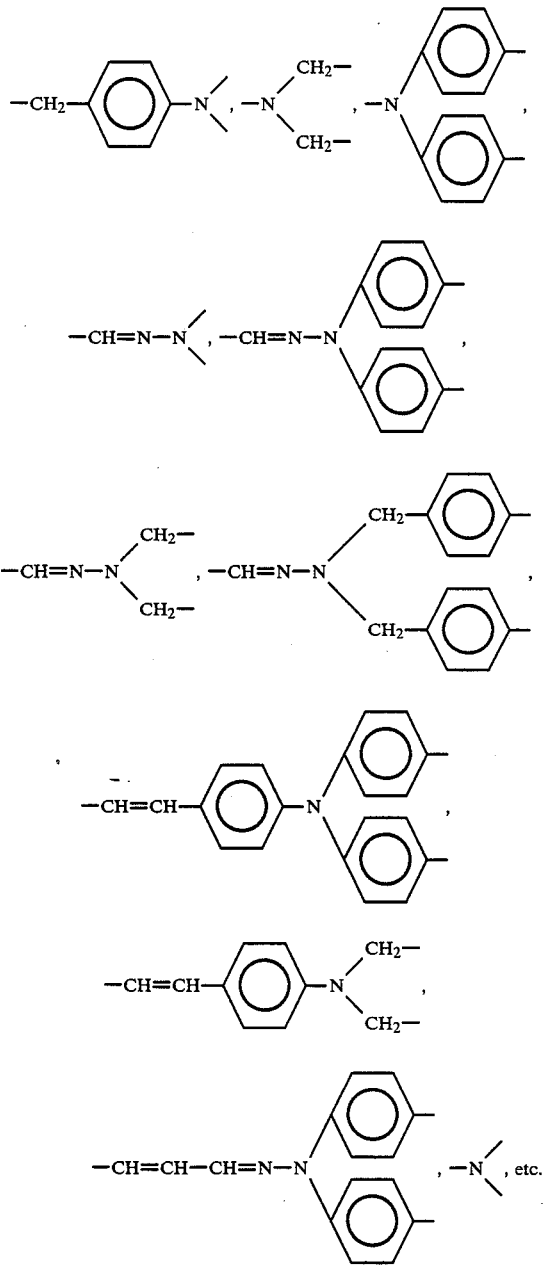

In the structure designated by (B), R$_4$ of the disulfide structure designated by (2), i.e., the chain disulfide structure represented by Formula (III) specifically represents an alkyl group such as methyl, ethyl, propyl or butyl, an aryl group such as phenyl, naphthyl, anthryl or biphenyl, an aralkyl group such as benzyl, phenethyl or naphthylmethyl. These groups may have the substituent as previously described.

The compound according to the present invention, having together the disubstituted aminoaryl group represented by Formula (I) and the chain disulfide structure represented by Formula (III), is constituted by combining the above disubstituted aminoaryl group with the chain disulfide structure moiety, but there are no particular limitations on the means for combining them. More specifically, the two structural moieties may be directly combined, or may be combined trough a conjugated or non-conjugated organic group, or further may be combined in the form in which aryl moieties or the like are covalently bonded, thereby exhibiting an excellent effect. In short, it is satisfactory if the disubstituted aminoaryl group and the chain disulfide structure moiety coexist in the same molecule.

The reason why this structure can bring about a specifically good effect against the deterioration of performances owing to repeated use is not clear, but it is presumed that the basicity of N of the disubstituted aminoaryl group and the d-orbital effect attributable to the two sulfur atoms, in disulfide cooperatively act on the environmental deterioration factors such as ozone, NO$_x$ and nitric acid, generated inside a copying machine, to prevent penetration of the environmental deterioration factors.

Among these compounds, the compound represented by the following general formula (VIII) is especially preferable.

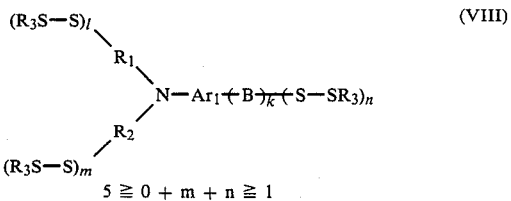

$$5 \geq 0 + m + n \geq 1$$

(VIII)

(wherein Q, m, n, k and B are the same as defined above.)

In the structure designated by (B), R$_5$ of the sulfide structures designated by (3), i.e., the chain sulfide structure represented by Formula (IV) and the chain sulfide structure represented by Formula (V), specifically represent an aryl group such as phenyl, naphthyl or biphenyl. R$_6$ thereof also specifically represents an alkyl group such as methyl, ethyl, propyl or butyl, an aryl group such as phenyl, naphthyl, anthryl or biphenyl, an aralkyl group such as benzyl, phenethyl or naphthylmethyl. These groups of R$_5$ and R$_6$ may have the substituent as previously described.

The compound according to the present invention, having together the disubstituted aminoaryl group represented by Formula (I) and the chain sulfide structure represented by Formula (IV) and chain sulfide structure represented by Formula (V), is constituted by combining the above disubstituted aminoaryl group with the aryl-substituted chain disulfide structure and chainlike sulfide structure moiety, but there are no particular limitations on the means for combining them. More specifically, the two structural moieties may be directly combined, or may be combined through a conjugated or non-conjugated organic group, or further may be combined in the form in which aryl moieties or the like are covalently bonded, thereby exhibiting an excellent effect. In short, it is satisfactory if the disubstituted aminoaryl group and the aryl-substituted chain disulfide structure and chain sulfide structure moiety coexist in the same molecule.

The reason why this structure can bring about a specifically good effect against the deterioration of performance owing to repeated use is not clear, but is presumed that the basicity of N of the disubstituted aminoaryl group and the d-orbital effect attributable to the sulfur atom in sulfide cooperatively act on the environmental deterioration factors such as ozone, NO$_x$ and nitric acid, generated inside a copying machine, to prevent penetration of the environmental deterioration factors.

No sufficient effect can be obtained if the aryl-substituted chain sulfide structure exists alone. This is presumably because, while the alkylthio group and aralkylthio group are influenced by electron donative groups resulting in reasonably activated sulfur atoms, the arylthio group is influenced by the aryl group resulting in a lower activity of sulfur atom as compared with the former two groups. Hence, one or more of additional sulfide structures are required to exist.

Among these compounds, the compound represented by the following general formula (XII) is especially preferable.

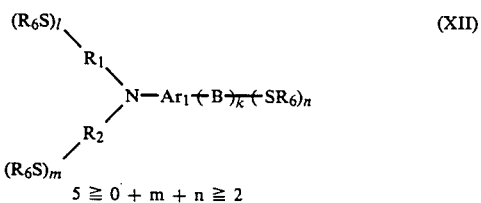

(wherein at least one of $R_6$ is $R_5$; and Q, m, n, k and B are the same as defined above.)

In the structure designated by (B), the sulfide structure designated by (4), i.e., the cyclic sulfide structure or cyclic disulfide structure containing two or more sulfur atoms specifically refers to a heterocyclic group having two or more of the structure —S— or one or more of the structure —S—S— and includes structures derived from the heterocyclic groups as exemplified by the following:

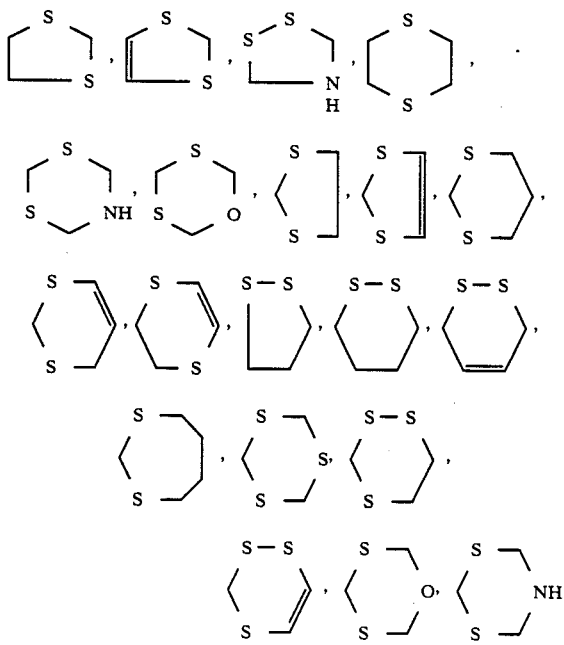

These structures may also contain a condensed aromatic ring.

The compound according to the present invention, having together the disubstituted aminoaryl group represented by Formula (I) and the cyclic sulfide structure or cyclic disulfide structure containing two or more sulfur atoms, is constituted by combining the above disubstituted aminoaryl group with the cyclic sulfide structure or cyclic disulfide structure moiety, but there are no particular limitations on the means for combining them. More specifically, the two structural moieties may be directly combined, or may be combined through a conjugated or non-conjugated organic group, or further may be combined in the form in which aryl moieties or the like are covalently bonded, thereby exhibiting an excellent effect. In short, it is satisfactory if the disubstituted aminoaryl group and the cyclic sulfide structure or cyclic disulfide structure moiety coexist in the same molecule. Provided that the cyclic sulfide having only one sulfur atom result in a weak effect, and hence is required to have two or more of sulfur atoms.

The reason why this structure can bring about a specifically good effect against the deterioration of performance owing to repeated use is not clear, but is presumed that the basicity of N of the disubstituted aminoaryl group and the d-orbital effect attributable to the sulfur atom in sulfide or disulfide cooperatively act on the environmental deterioration factors such as ozone, $NO_x$ and nitric acid, generated inside a copying machine, to prevent penetration of the environmental deterioration factors.

Among these compounds, the compound represented by the following general formula (XI) is especially preferable.

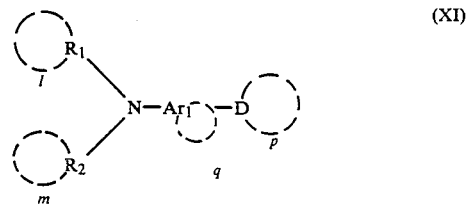

(wherein ◯ represents a cyclic sulfide structure or cyclic disulfide structure having two or more sulfur atoms; Q, m, p and q represent a number of the cyclic structure and an integer of 0, 1 or 2; and D represents a tri-valent hydrocarbon group, a tri-valent hydrocarbon having one or two of a nitrogen atom or a tri-valent nitrogen atom group, and specifically, includes the tri-valent groups, etc., among the examples of B mentioned above.)

In the compound represented by Formula (VI), examples of $R_1$ and $R_2$ are the same as defined for $R_1$ and $R_2$ described above.

$Ar_2$ represents a divalent heterocyclic group derived from an arylene group such as phenylene, naphthylene, anthrilene, biphenylene or phenanthrylene, or pyridine, quinoline, indole, carbazole, thiophene, benzothiophene, acrydine, phenothiazine, phenoxazine, phenazine, benzofuran, dibenzofuran, benzoxazole, benzothiazole, benzotriazole, oxadiazole or oxathiadiazole, etc.

X and Y have a thioether structure on one or both of them. Examples of the $R_7$, $R_8$, $R_9$, alkyl group, aralkyl group and aryl group are the same as the examples of the alkyl group, aralkyl group and aryl group in $R_1$ and $R_2$ previously described.

Examples of the thioester ring formed by the combination of X with Y include the following:

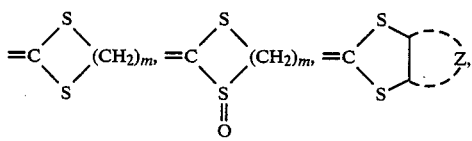 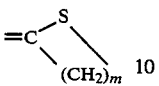

(m represents an integer of 2, 3 or 4, and Z represents an aromatic ring.)

In the compound represented by Formula (VI), the alkyl group, aralkyl group, aryl group, arylene group and divalent heterocyclic group may have a substituent, and such a substituent includes the substituents previously described, as well as an alkylthio group such as methylthio, ethylthio or butylthio, an aralkylthio group such as benzylthio or phenethylthio, or an arylthio group such as a phenylthio, naphthylthio or biphenylthio.

The reason why this structure can bring about a specially good effect against the deterioration of performances owing to repeated use is not clear, but it is presumed that the basicity of N of $$\begin{array}{c} R_1 \\ \diagdown \\ N \\ \diagup \\ R_2 \end{array}$$

and the d-orbital effect attributable to the sulfur atom in the thioether structure cooperatively act on the environmental deterioration factors such as ozone, $NO_x$ and nitric acid, generated inside a copying machine, to prevent penetration of the environmental deterioration factors. Provided that this effect can be small when one of X and Y is a hydrogen atom.

The effect can be particularly remarkable especially when, among these compounds, in Formula (VI), $Ar_2$ represents phenylene and two thioether structures are present such that both X and Y are thioether structures each represented by $S-R_3$ or are residual groups necessary to form by the combination thereof a thioether ring posessing two thioether structures.

Typical examples of the compound according to the present invention are mentioned below.

1. Examples of the compound having together the disubstituted aminoaryl group represented by Formula (I) and the chainlike sulfide structure represented by Formula (II):

1-1.

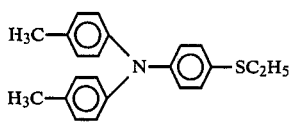

1-2.

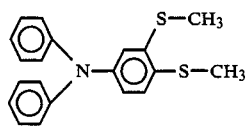

1-3.

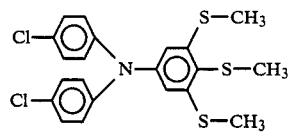

1-4.

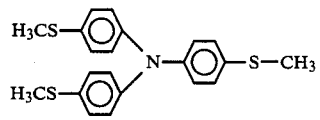

1-5.

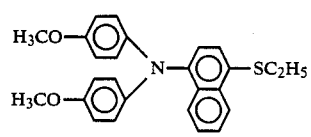

1-6.

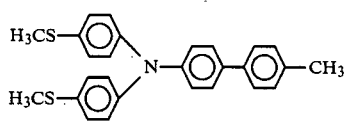

1-7.

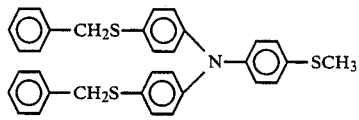

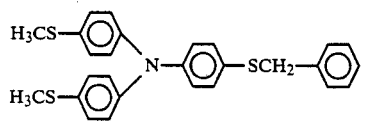
1-8.
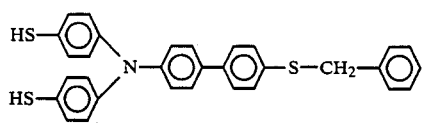
1-9.
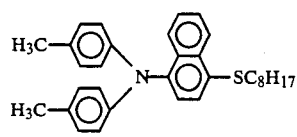
1-10.
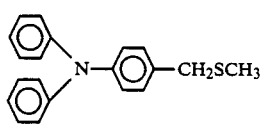
1-11.
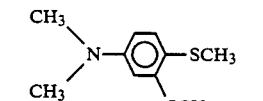
1-12.
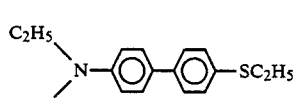
1-13.
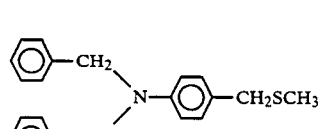
1-14.
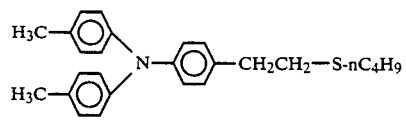
1-15.
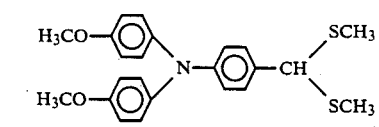
1-16.
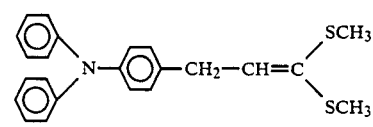
1-17.
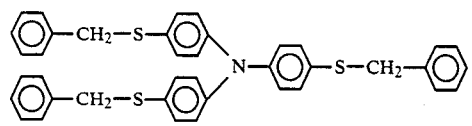
1-18.
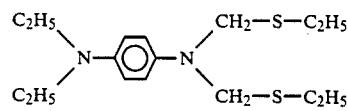
1-19.

-continued
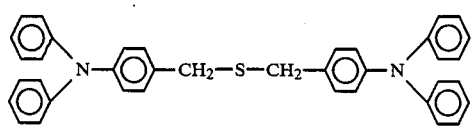
1-20.
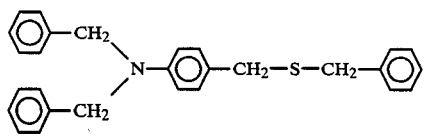
1-21.
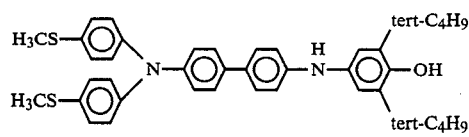
1-22.
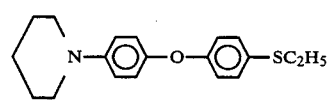
1-23.
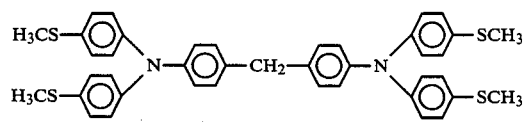
1-24.
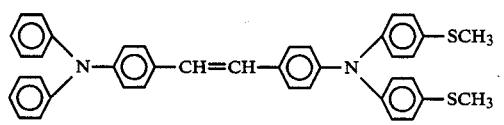
1-25.
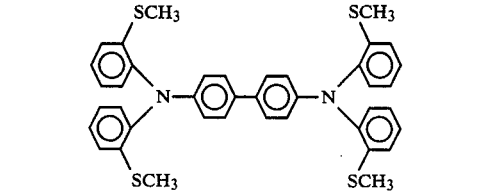
1-26.
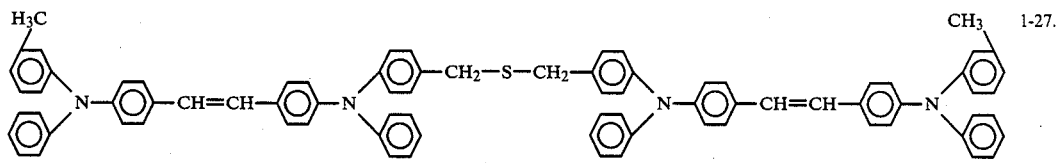
1-27.
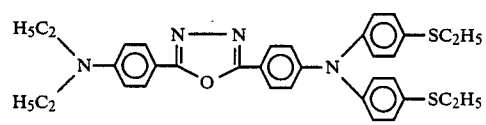
1-28.
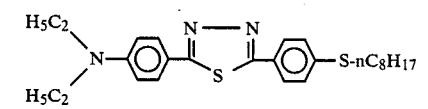
1-29.
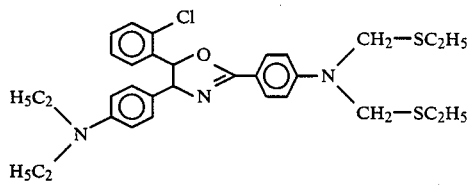
1-30.

-continued
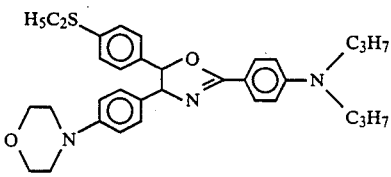
1-31.
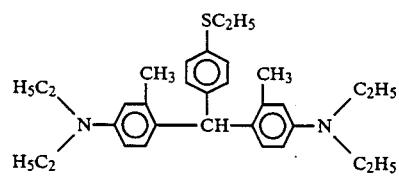
1-32.
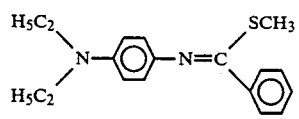
1-33.
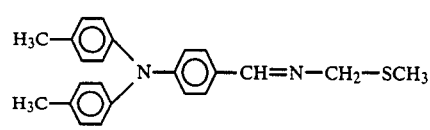
1-34.
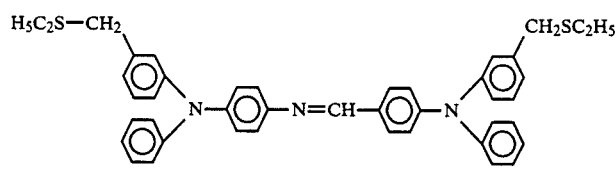
1-35.
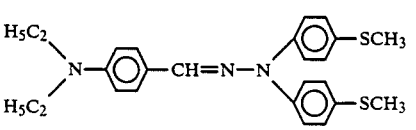
1-36.
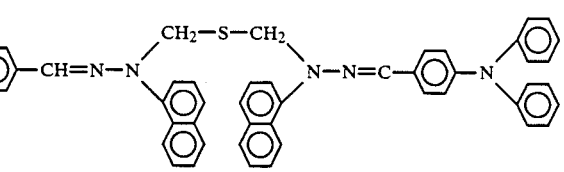
1-37.
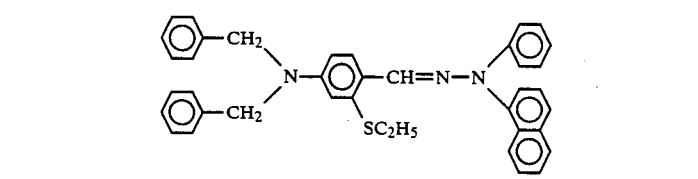
1-38.
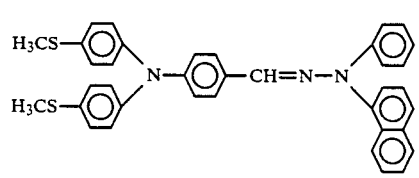
1-39.
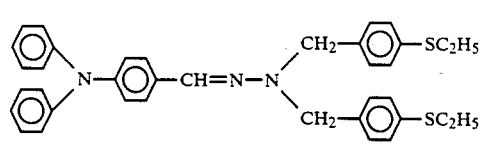
1-40.

-continued

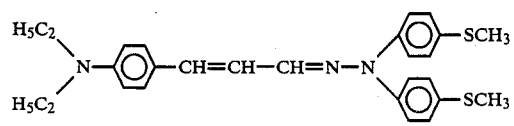
1-41.

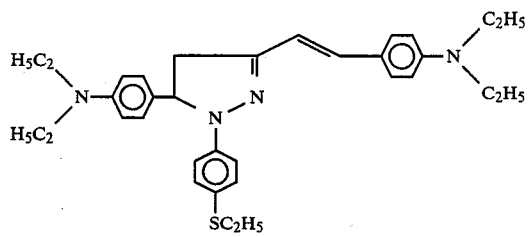
1-42.

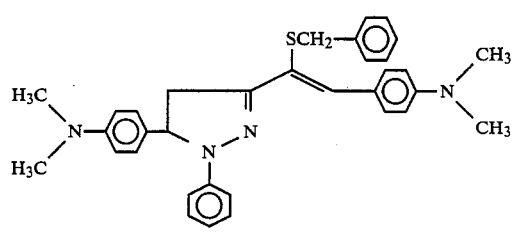
1-43.

These compounds can be synthesized by commonly available methods, or their similar methods, for synthesizing sulfides or tertiary amines through the synthesis routes that may vary depending on their structural formulas.

2. Examples of the compound having together the disubstituted aminoaryl group represented by Formula (I) and the chain disulfide structure represented by Formula (III):

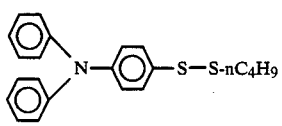
2-1.

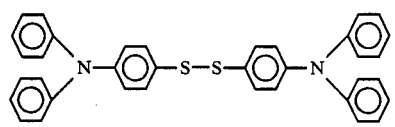
2-2.

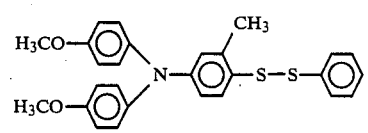
2-3.

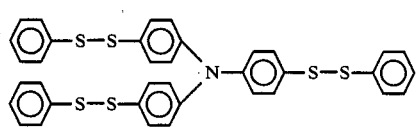
2-4.

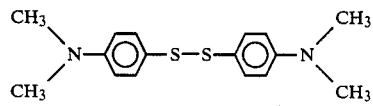
2-5.

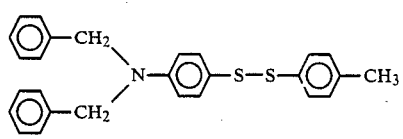
2-6.

-continued
2-7. 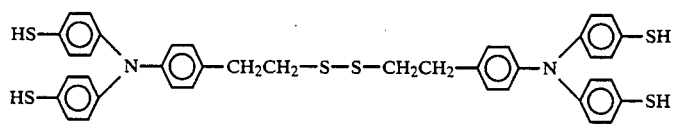
2-8. 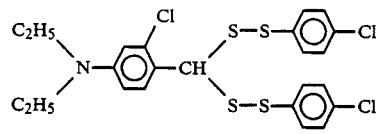
2-9. 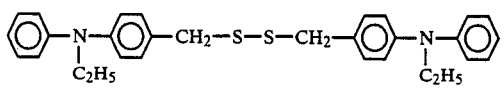
2-10. 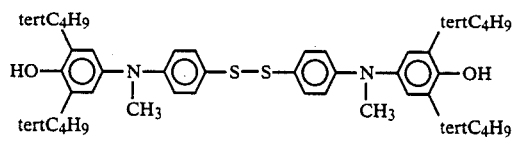
2-11. 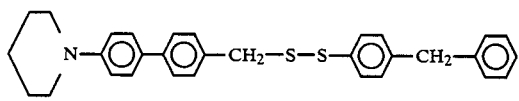
2-12. 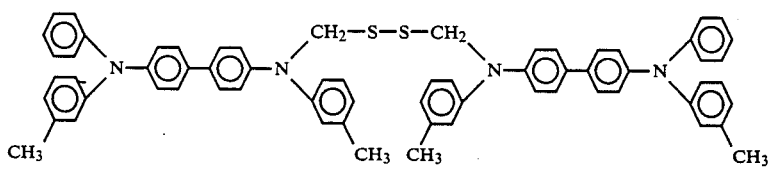
2-13. 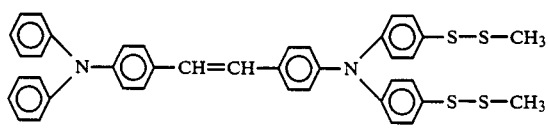
2-14. 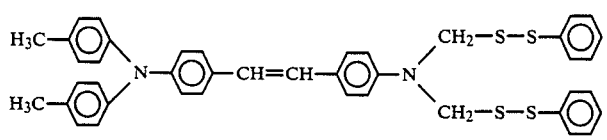
2-15. 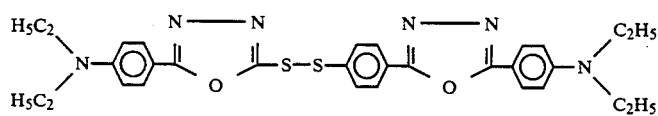
2-16. 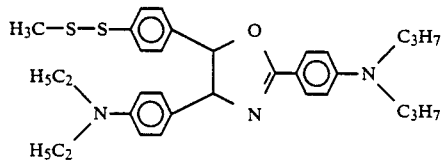
2-17. 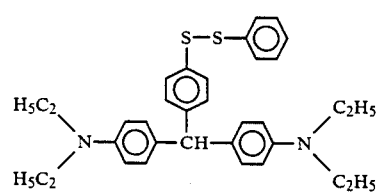

-continued

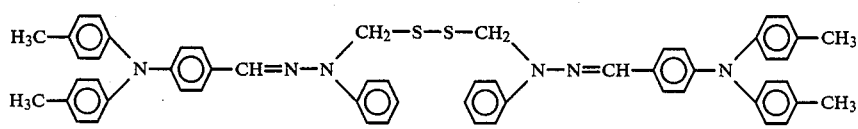
2-18.

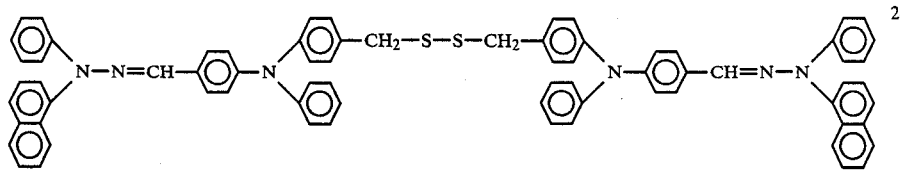
2-19.

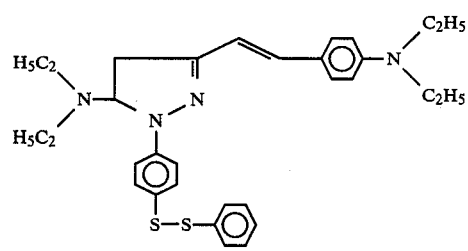
2-20.

These compounds can be synthesized by commonly available methods, or their similar methods, for synthesizing disulfides or tertiary amines through the synthesis routes that may vary depending on their structural formulas.

3. Examples of the compound having together the disubstituted aminoaryl group represented by Formula (I) and the chain disulfide structure represented by Formula (IV) and chain sulfide structure represented by Formula (V).

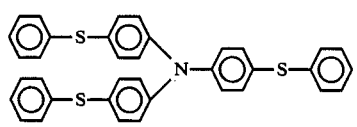
3-1.

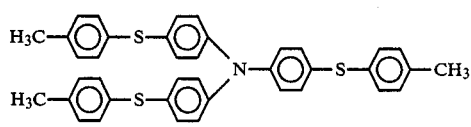
3-2.

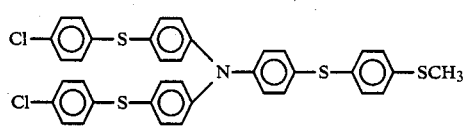
3-3.

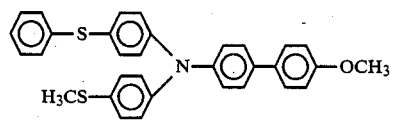
3-4.

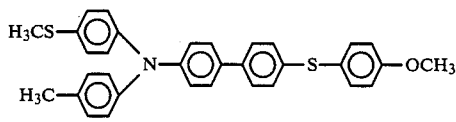
3-5.

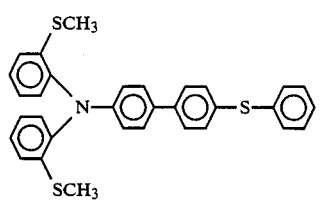
3-6.

-continued
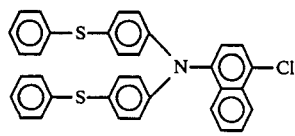 3-7.
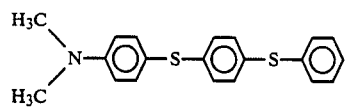 3-8.
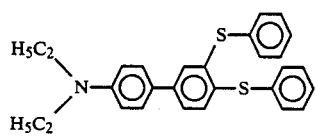 3-9.
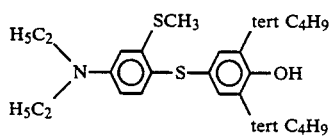 3-10.
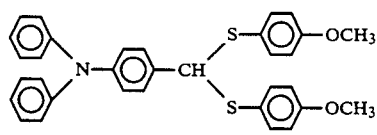 3-11.
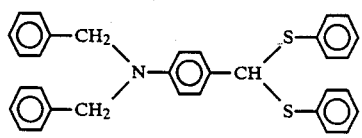 3-12.
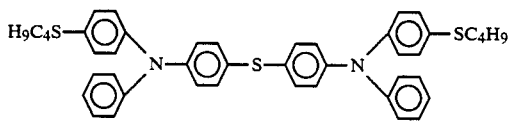 3-13.
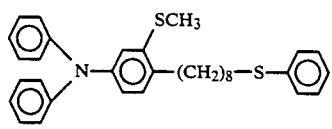 3-14.
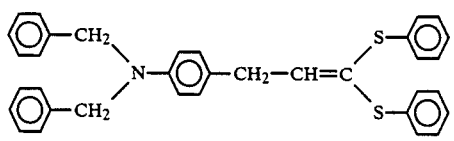 3-15.
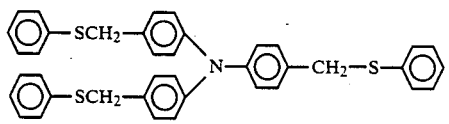 3-16.
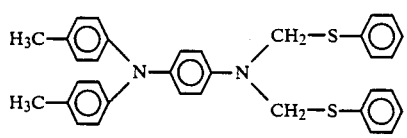 3-17.

-continued
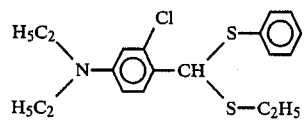
3-18.
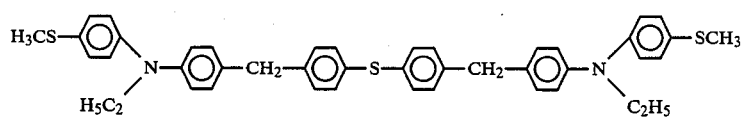
3-19.
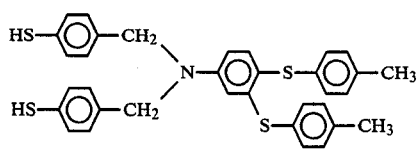
3-20.
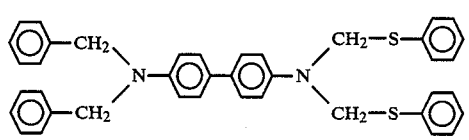
3-21.
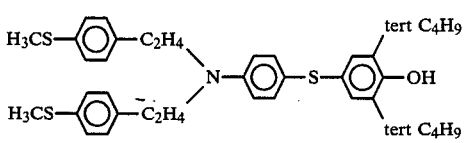
3-22.
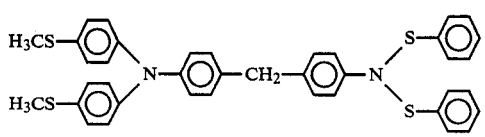
3-23.
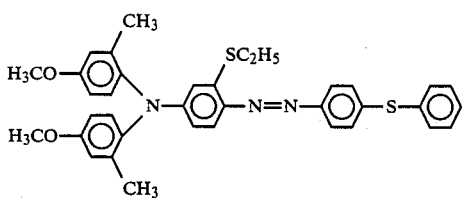
3-24.
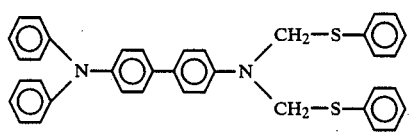
3-25.
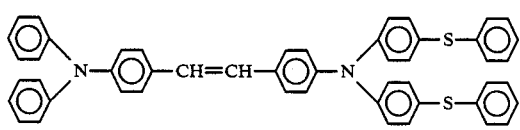
3-26.
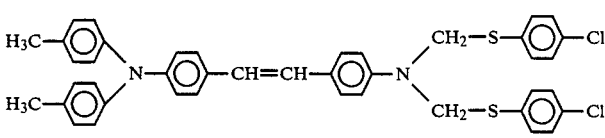
3-27.

-continued
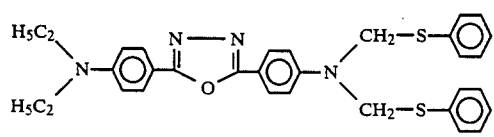
3-28.
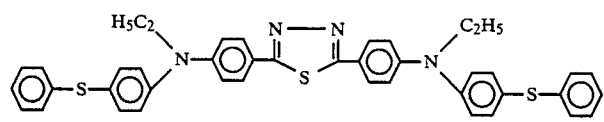
3-29.
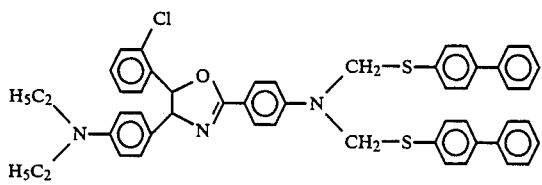
3-30.
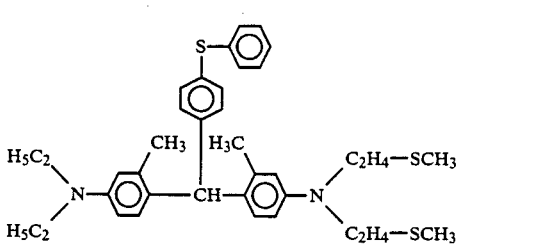
3-31.
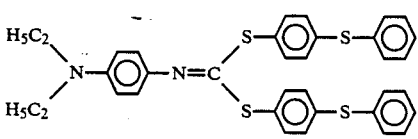
3-32.
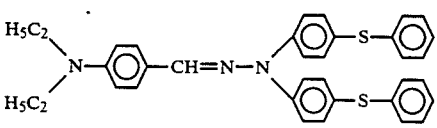
3-33.
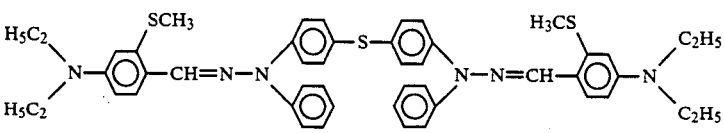
3-34.
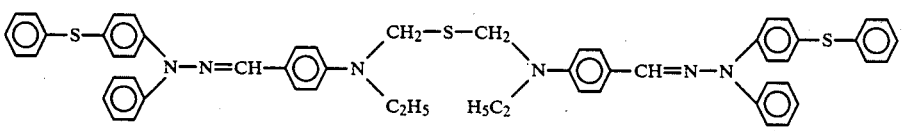
3-35.
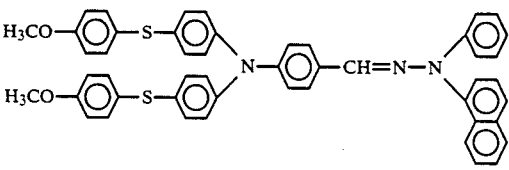
3-36.
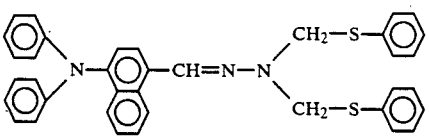
3-37.

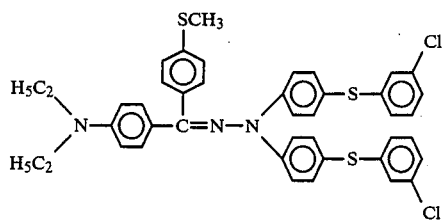

3-38.

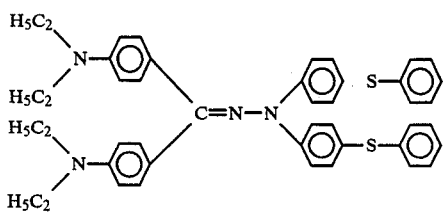

3-39.

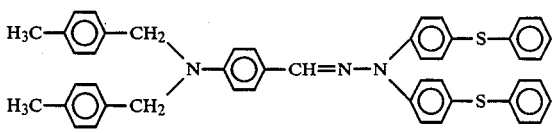

3-40.

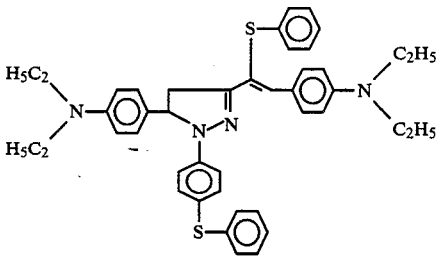

3-41.

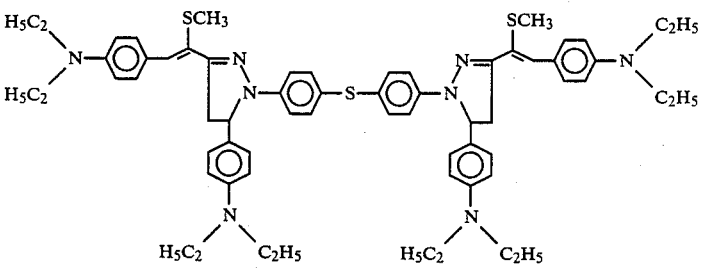

3-42.

These compounds can be synthesized by commonly available methods, or their similar methods, for synthesizing sulfides or tertiary amines through the synthesis routes that may vary depending on their structural formulas.

4. Examples of the compound having together the disubstituted aminoaryl group represented by Formula (I) and the cyclic sulfide structure or cyclic disulfide structure containing two or more sulfur atoms.

4-1.

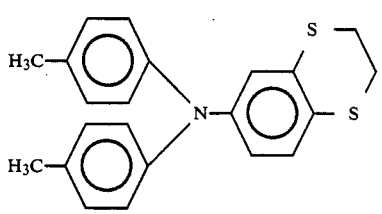

-continued
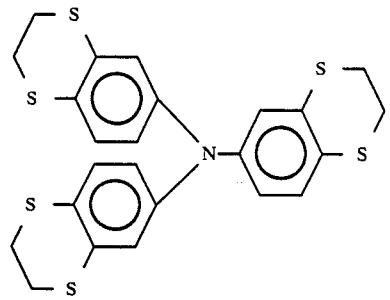
4-2.
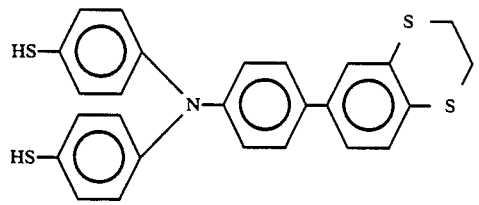
4-3.
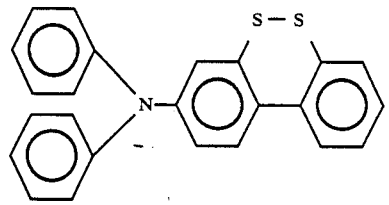
4-4.
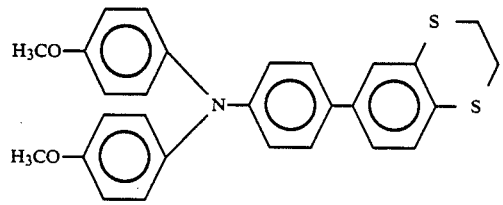
4-5.
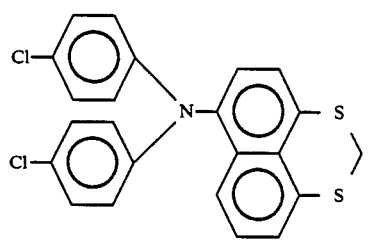
4-6.
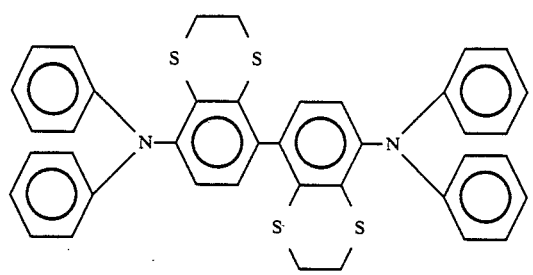
4-7.

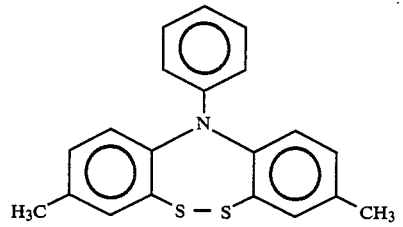
4-8.
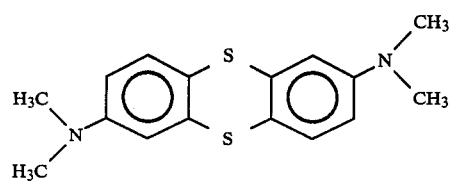
4-9.
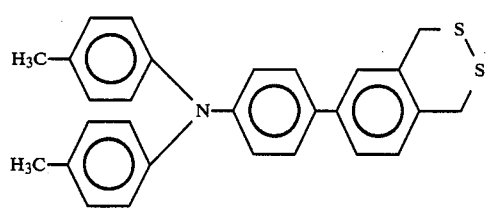
4-10.
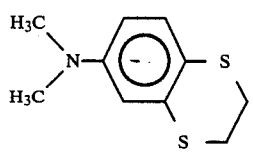
4-11.
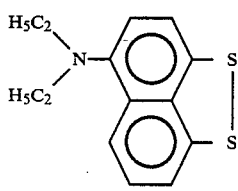
4-12.
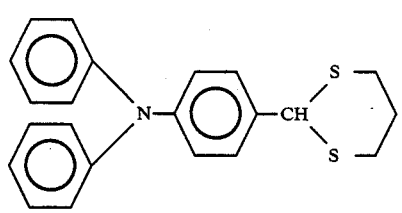
4-13.
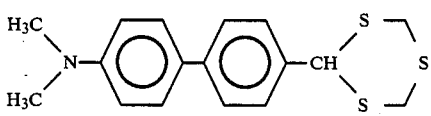
4-14.
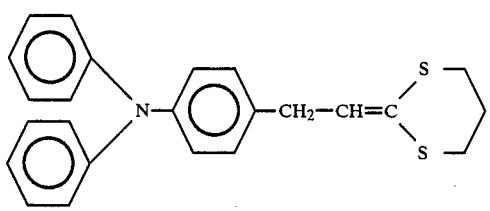
4-15.

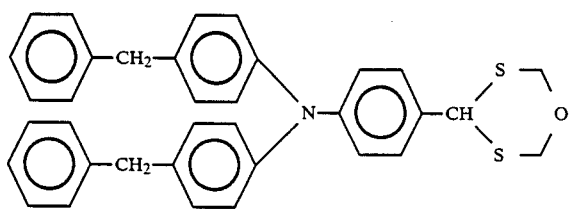
4-16.
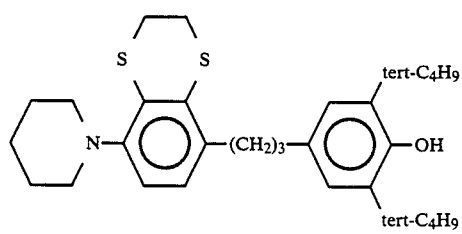
4-17.
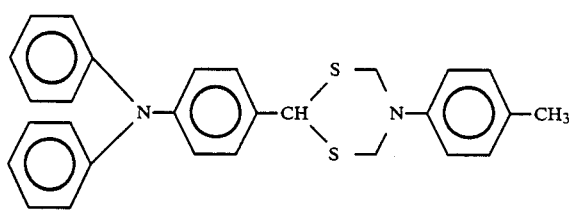
4-18.
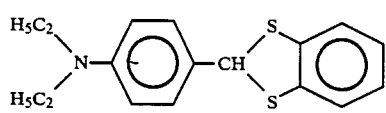
4-19.
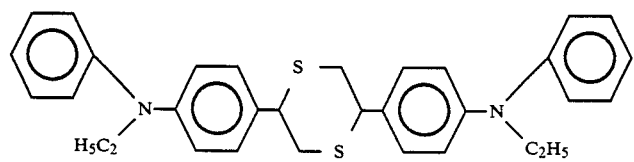
4-20.
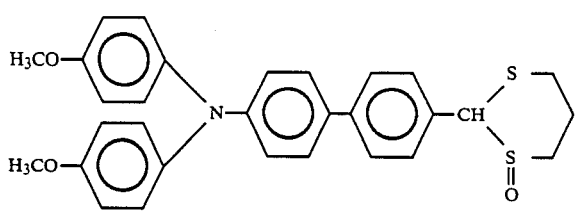
4-21.
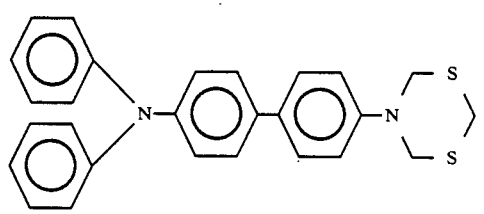
4-22.
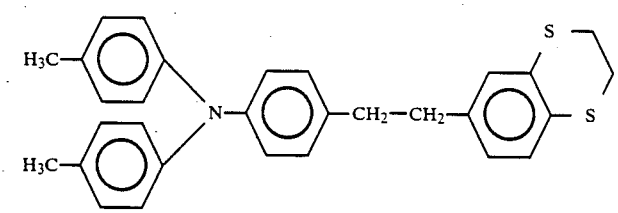
4-23.

-continued
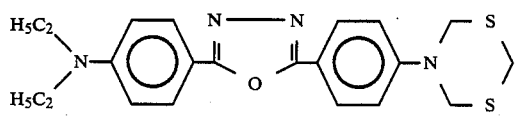
4-24.
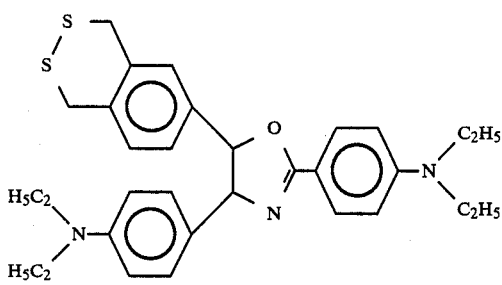
4-25.
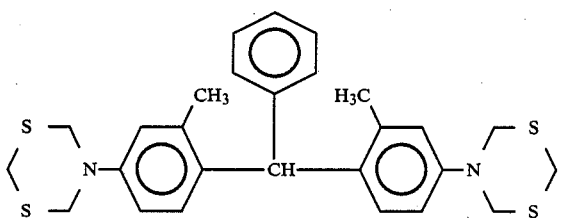
4-26.
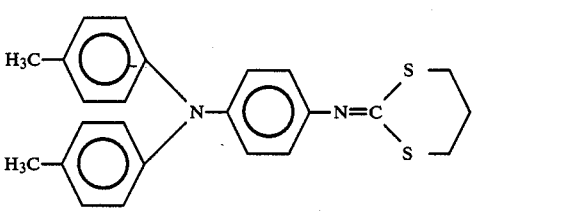
4-27.
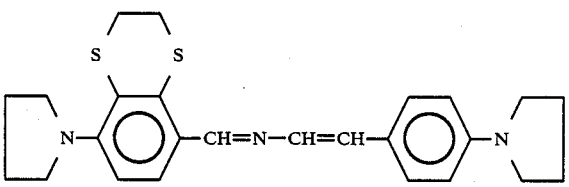
4-28.
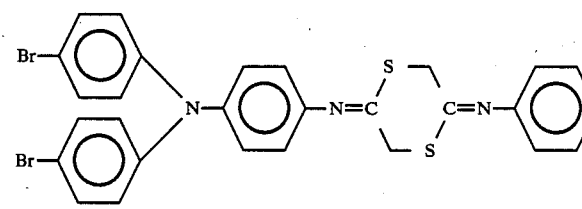
4-29.
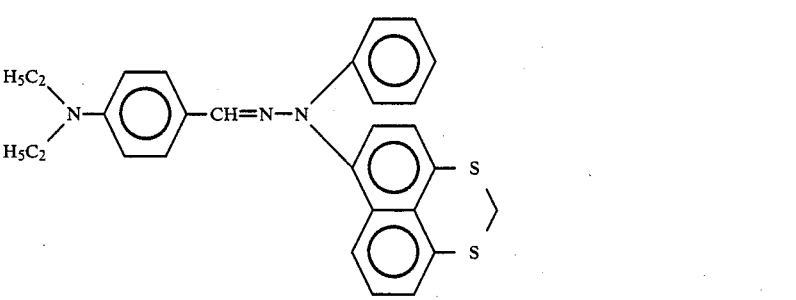
4-30.

4-31.
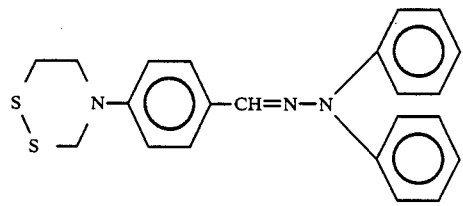
4-32.
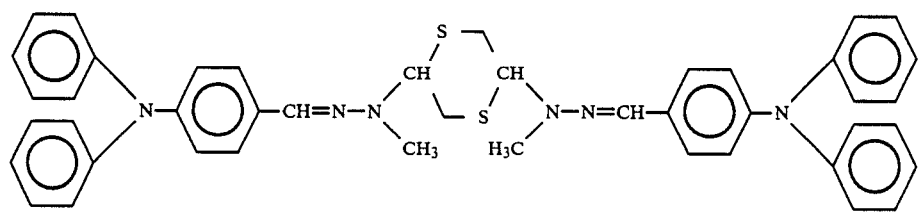
4-33.
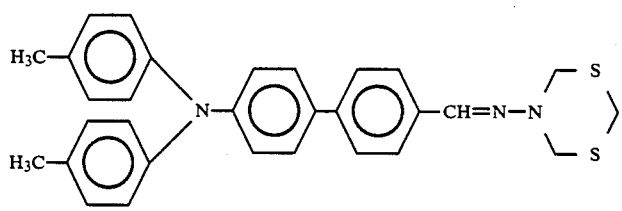
4-34.
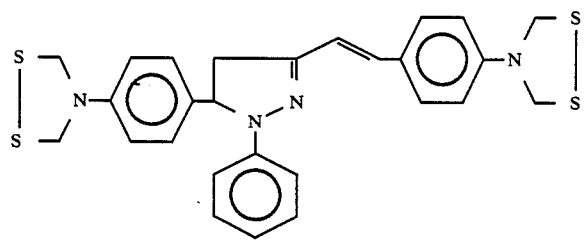
4-35.
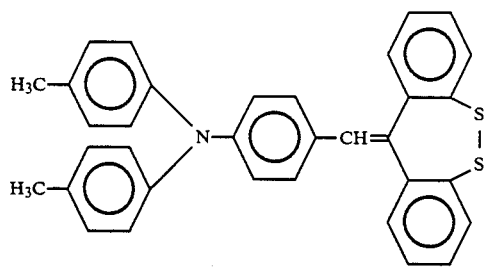
These compounds can be synthesized by commonly available methods, or their similar methods, for synthesizing cyclic sulfides, cyclic disulfides or tertiary amines through the synthesis routes that may vary depending on their structural formulas.
5. Examples of the compound represented by Formula (VI):
5-1.
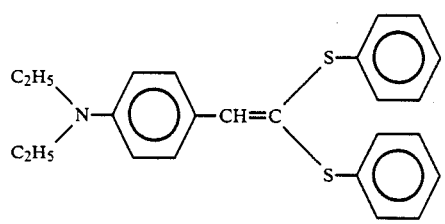

-continued
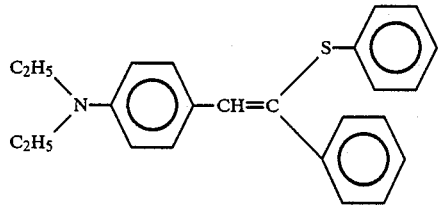 5-2.
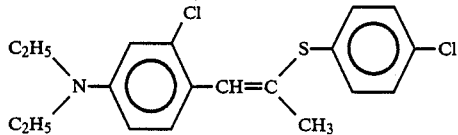 5-3.
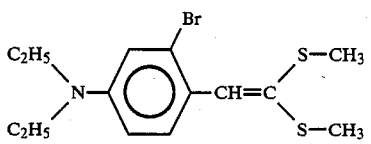 5-4.
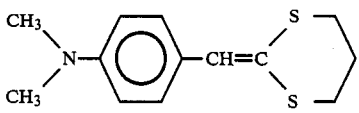 5-5.
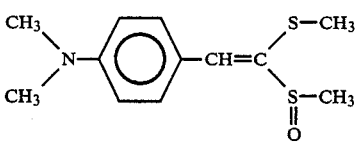 5-6.
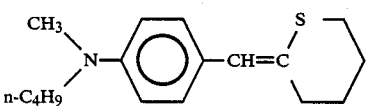 5-7.
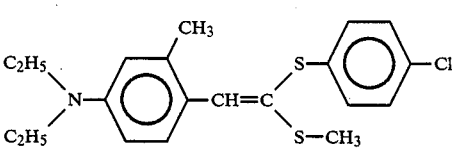 5-8.
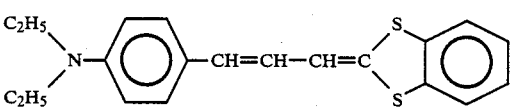 5-9.
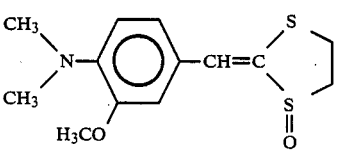 5-10.
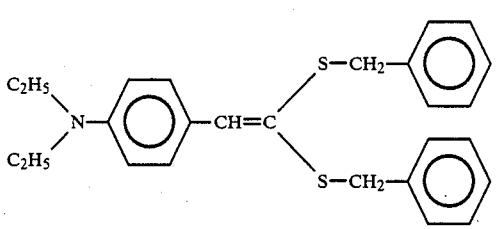 5-11.

-continued
5-12.
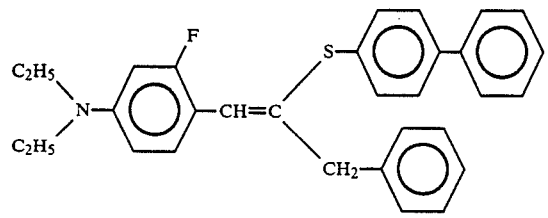
5-13.
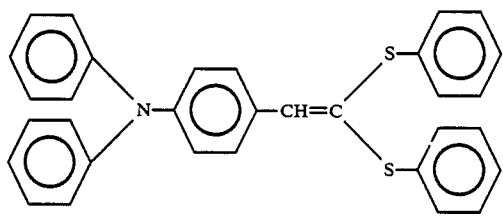
5-14.
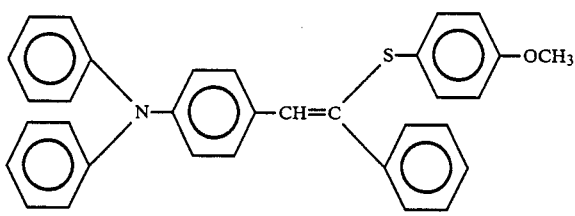
5-15.
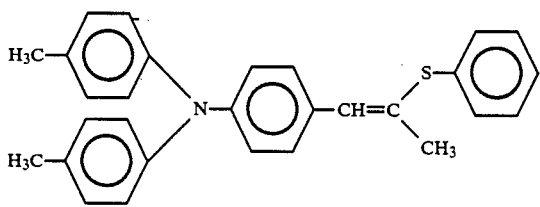
5-16.
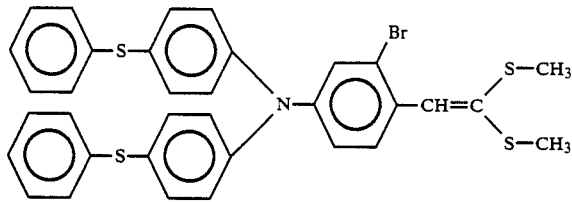
5-17.
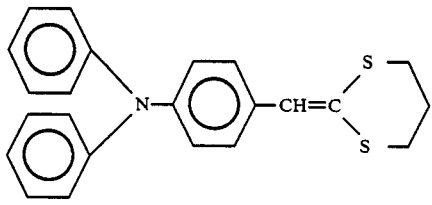
5-18.
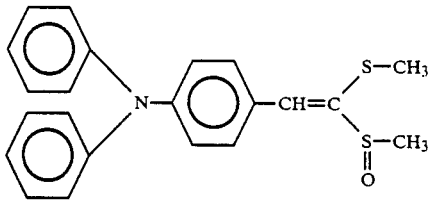

5-19.
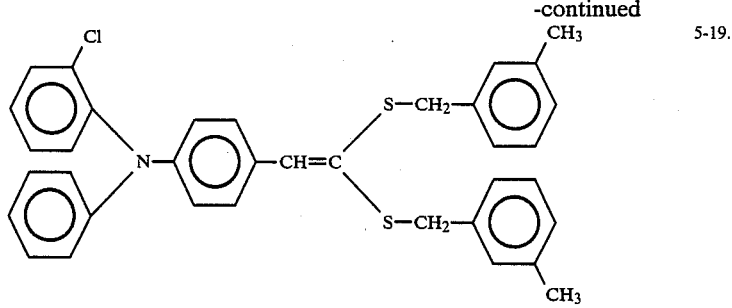
5-20.
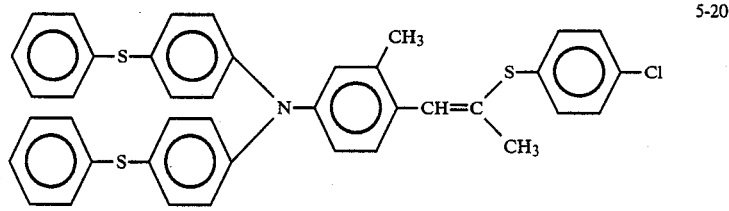
5-21.
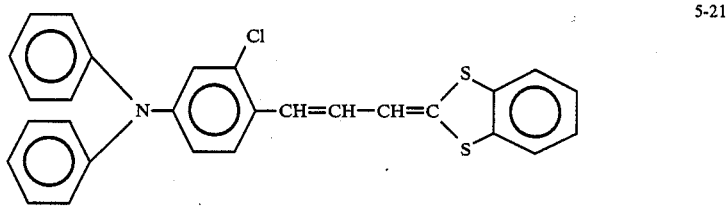
5-22.
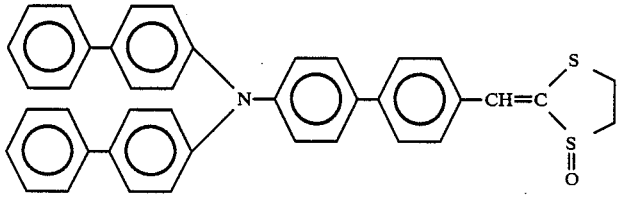
5-23.
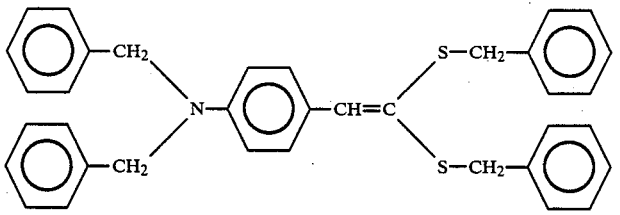
5-24.
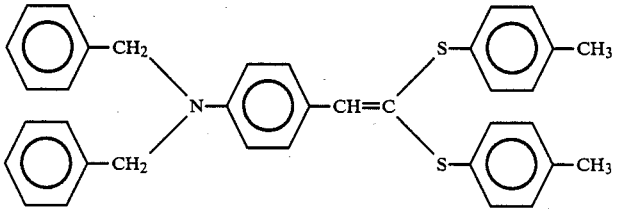
5-25.
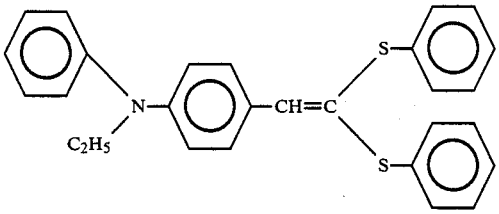

5-26.
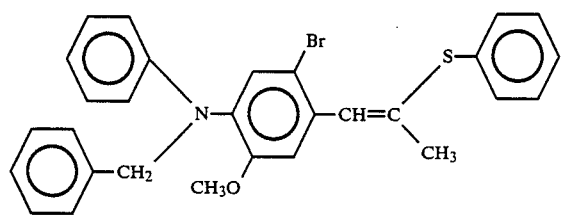
5-27.
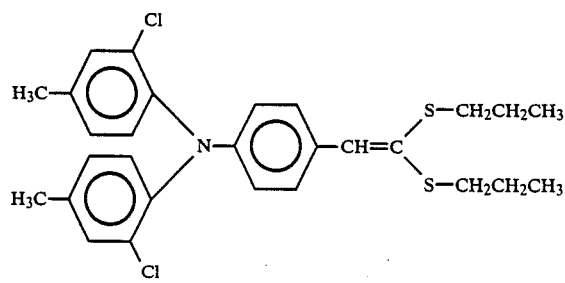
5-28.
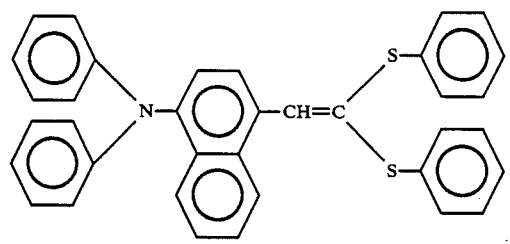
5-29.
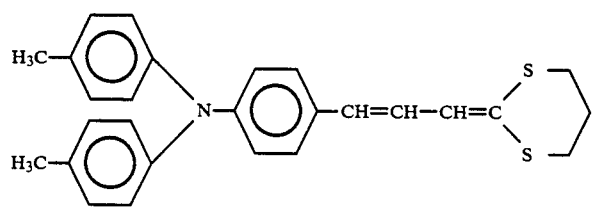
5-30.
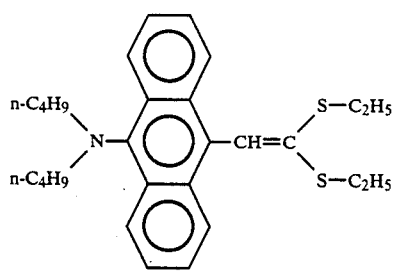
5-31.
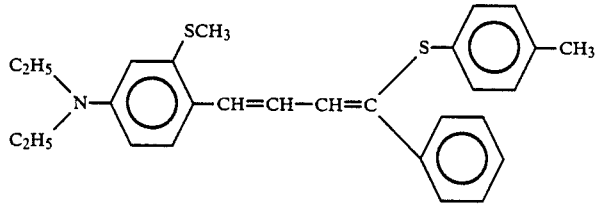
5-32.
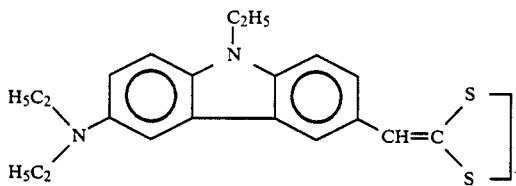

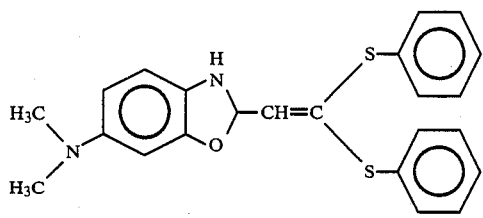
5-33.
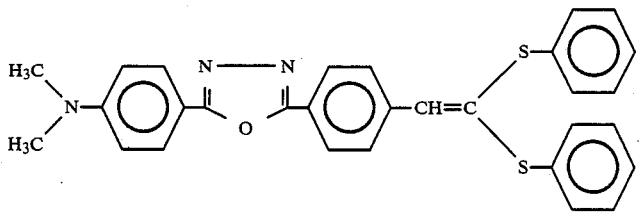
5-34.
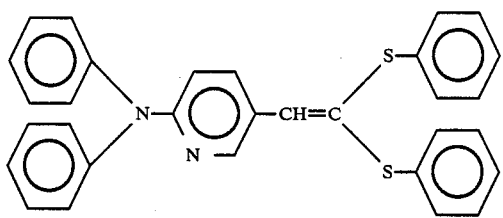
5-35.
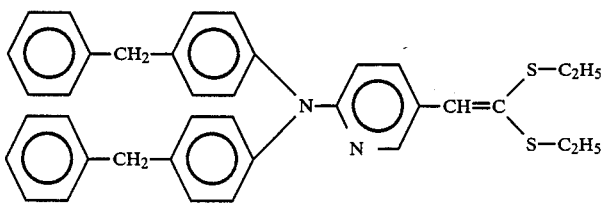
5-36.
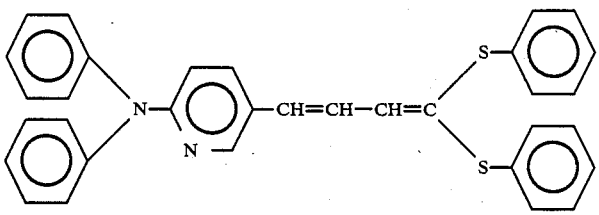
5-37.
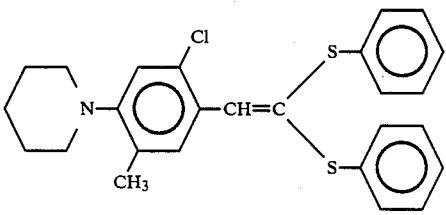
5-38.
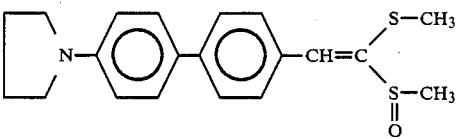
5-39.

5-40.

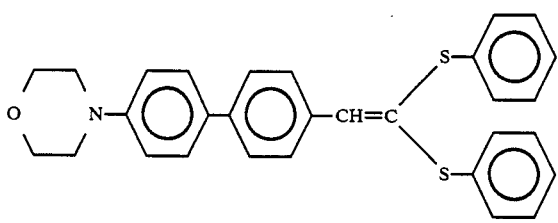

These compounds can be synthesized, for example, in the following manner:

(Synthesis method for Exemplary Compound No. 5-17)

Under a nitrogen stream, 23 g (187 mmol) of trimethyl phosphite and 3.4 g (22 mmol) of trithio carbonate having the following structure:

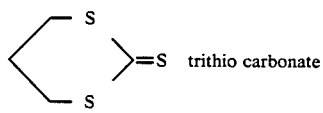 trithio carbonate are reacted by heating to 55° C. with stirring for 3 hours. Next, 5.4 g (20 mmol) of p-diphenylaminobenzaldehyde dissolved in 35 g of methylene chloride is added to continue the reaction at 55° C. for 15 hours. Subsequently, the reaction mixture is once evaporated to dryness under reduced pressure and thereafter recrystalization is carried out twice using a methylene chloride/petroleum ether mixed solvent to obtain 5.3 g of a final product in the form of yellowish white crystals.

Yield: 71%; m.p.: 132° to 133° C.

| | Elementary analysis: | |
|---|---|---|
| | Calculated | Found |
| C | 73.56 | 73.59 |
| H | 5.64 | 5.60 |
| N | 3.73 | 3.76 |

The compounds other than the compound in the above synthesis example can also be synthesized by methods similar thereto or by a method comprising dehydration condensation of a corresponding aldehyde with dithioether having an active methylene group such

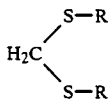

A layer constitution of the electrophotographic photosensitive member of the present invention is shown in FIG. 1. The electrophotographic photosensitive member comprises a conductive support 1 provided thereon with photosensitive layer 2.

The compound according to the present invention can particularly exhibit its effect when, in a layer-separated photosensitive layer comprising a charge generation layer 3 and a charge transport layer 4 as illustrated in FIG. 1A, contained in the charge generation layer 2 or the charge transport layer 3. In particular, it can exhibit a remarkable effect on a charge transporting material in the photosensitive layer.

Figure 1B:
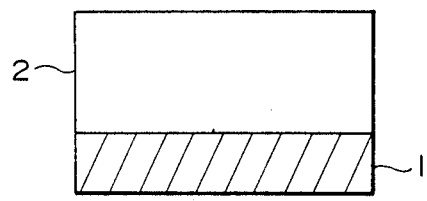

Also, many compounds according to the present invention have the carrying performances of carriers in themselves as charge transporting materials, and may be used alone without being mixed with other charge transporting materials described below. The charge generation layer 3 may also be laminated on the charge transport layer 4. The compound according to the present invention may also be contained in a single layer type photosensitive layer as illustrated in FIG. 1B.

The charge transporting material used together with the compound according to the present invention comprises an organic photoconductive material comprising an electron transporting material or a positive hole transporting material. The electron transporting material includes electron attractive materials such as chloranil, bromoanil, tetracyanoethylene, tetracyanoquinodimethane, 2,4,7-trinitro-9-fluolenone, 2,4,5,7-tetranitro-9-fluolenone, 2,4,7-trinitro-9-dicyanometylenefluolenone, 2,4,5,7-tetranitroxanthone and 2,4,8-trinitrothioxanthone, or those obtained by forming these electron attractive materials into polymers.

The positive hole transporting material includes hydrazone compounds such as pyrene, N-ethylcarbazole, N-isopropylcarbazole, N-methyl-N-phenylhydrazino-3-methylidene-9-ethylcarbazole, N,N-diphenylydrazino-3-methylidene-9-ethylcarbazole, N,N-diphenylhydrazino-3-methylidene-10-ethylphenothiazine, N,N-diphenylhydrazino-3-methylidene-10-ethylphenoxazine, p-diethylaminobenzaldehydo-N,N-diphenylhydrazone, p-diethylaminobenzaldehydo-N-α-naphthyl-N-phenylhydrazone, p-pyrolidinobenzaldehydo-N,N-diphenylhydrazone, 1,3,3-trimethylindolenine-ω-aldehydo-N,N-diphenylhydrazone and p-diethylbenzaldehydro-3-metylbenzthiazoline-2-hydrazone, pyrazoline compounds such as 2,5-bis(p-diethylaminophenyl)-1,3,4-oxadiazole, 1-phenyl-3-(p-diethylaminostyryl)-5-(p-diethylaminophenyl) pyrazoline, 1-[quinolyl(2)]-3-(p-diethylaminostyryl)-5-(p-diethylaminophenyl)-pyrazoline, 1-[pyridyl(2)]-3-p-diethylaminostyryl)-5-(p-diethylaminophenyl) pyrazoline, 1-[6-methoxy-pyridyl(2)]-3-(p-diethylaminostyryl)-5-(p-diethylaminophenyl) pyrazoline, 1-[pyridyl(3)]-3-(p-diethylaminostyryl)-5-(p-diethylaminophenyl)pyrazoline, 1-[lepidyl(2)]-3-(p-diethylaminostyryl)-5-(p-diethylaminophenyl) pyrazoline, 1-[pyridyl(2)]-3-(p-diethylaminostyryl)-4-methyl-5-(p-diethylaminophenyl)-pyrazoline, 1-[pyridyl(2)]-3-(α-methyl-p-diethylaminostyryl)-5-(p-diethylaminophenyl)pyrazoline, 1-phenyl-3-(p-diethylaminostyryl)-4-methyl-5-(p-diethylaminophenyl) pyrazoline, 1-phenyl-3-(α-benzyl-p-diethylaminostyryl)-5-(p-diethylaminophenyl) pyrazoline and spiropyrazoline, styryl compounds such as α-phenyl-4-N,N-diphenylaminostilbene, N-ethyl-3-(α-phenylstyryl)carbazole, 9-p-dibenzylaminobenzyl-idene-9H- fluorenone and 5-p-ditolylaminobenzilidene-5H-dibenzo[a,d]cycloheptene, oxazole compounds such as 2-(p-diethylaminostyryl)-6-diethylaminobenzoxazole and 2-(p-diethylaminophenyl)-4-(p-dimethylaminophenyl)-5-(2-chlorophenyl)oxazole, thiazole compounds such as 2-(p-diethylaminostyryl)-6-diethylaminobenzothiazole, triarylmethane compounds such as bis(4-diethylamino-2-methylphenyl)-phenylmethane, polyarylalkanes such as 1,1-bis(4-N,N-dietylamino-2-methylphenyl)heptane and 1,1,2,2-tetrakis(4-N,N-dimethylamino-2-methylphenyl) ethane, triphenylamine, poly-N-vinyl carbazole, polyvinyl pyrene, polyvinyl anthracene, polyvinyl acrydine, poly-9-vinyl phenylanthracene, pyreneformaldehyde resin and ethylcarbazole formaldehyde resin.

These charge transporting materials can be used alone or in combination of two or more.

The charge transport layer in the layer-separated electrophotographic photosensitive member according to the present invention may preferably be formed by coating a solution obtained by dissolving the above compound having together the disubstituted aminoaryl group and sulfide structure in the structural formula, in a suitable solvent together with the above charge transporting material and a binder, followed by drying. As previously described, the compound according to the present invention may be used simply together with the binder when it has the function as the charge transporting material. The binder used here may include, for example, polyarylate resins, polysulfone resins, polyamide resins, acrylic resins, acrylontrile resins, methacrylic resins, vinyl chloride resins, vinyl acetate resins, phenolic resins, epoxy resins, polyester resins, alkyd resins, polycarbonates, polyurethanes, or copolymer resins as exemplified by a styrene/butadiene copolymer, a styrene/acrylonitrile copolymer and a styrene/maleic acid copolymer. In addition to insulating polymers like these, it is also possible to use organic photoconductive polymers such as polyvinyl carbazole, polyvinyl anthracene and polyvinyl pyrene.

These binder and charge transporting material may be mixed preferably in such a proportion that the charge transporting material may comprise from 10 to 500 parts by weight based on 100 parts by weight of the binder.

The charge transport layer is electrically connected with the charge generation layer described below, and has functions to receive charge carriers injected from the charge generation layer in the presence of an electric field and transport the charge carriers to the surface. In this occasion, this charge transport layer may be laminated on the charge generation layer, or may otherwise be laminated beneath it. However, the charge transport layer may desirably laminated on the charge generation layer. This charge transport layer has a limit in the capability of transporting charge carriers, and therefore can not be made to have an unnecessarily large film thickness. In general, it may have a thickness of from 5 μm to 40 μm, but preferably in the range of from 10 μm to 30 μm.

The organic solvent used when such a charge transport layer is formed may vary depending on the type of the binders to be used, and may preferably be selected from those which may not dissolve the charge generation layer and the subbing layer described below. Usable as specific organic solvents are alcohols such as methanol, ethanol and isopropanol, ketones such as acetone, methyl ethyl ketone and cyclohexane, amides such as N,N-diemthylformamide, N,N-dimethylacetamide, sulfoxides such as dimethylsulfoxide, ethers such as tetrahydrofuran, dioxane and ethylene glycol monomethyl ether, esters such as methyl acetate and ethyl acetate, aliphatic halogenated hydrocarbons such as chloroform, methylene chloride, dichloroethylene, carbon tetrachloride and trichloroethylene, or aromatics such as benzene, tolene, xylene, monochlorobenzene and dichlorobenzene.

The coating can be carried out by using coating methods such as dip coating, spray coating, Meyer bar coating and blade coating. The drying may preferably be carried out be a method comprising bringing a coating into dryness to the touch at room temperature followed by heat drying. The heat drying can be carried out generally at a temperature of from 30° C. to 200° C., in a time ranging from 5 minutes to 2 hours, and in still air or under air blow.

The charge transport layer can be made to contain various additive and put into use. For example, they may include plasticizers such as diphenyl, m-terphenyl and dibutyl phthalate, surface lubricants such as silicone oils, grafted silicone polymers and various fluorocarbons, potential stabilizers such as dicyanovinyl compounds and carbazole derivatives, antioxidants such as β-carotene, Ni complexes and 1,4-diazabicyclo[2,2,2] octane.

The charge generation layer used in the present invention can be used as a deposited layer or as a coated layer by using alone or in combination the materials selected from inorganic charge generating materials such as selenium, selenium-tellurium, and amorphous silicon, cationic dyes such as pyrylium dyes, thiapyrylium dyes, azlenium dyes, thiacyanine dyes, quinocyamine dyes and azulenium dyes, polycyclic quinone pigments such as anthanthrone pigments, dibenzpyrenequinone pigments and pyranthrone pigments, suqualilium salt dyes, phthalocyanine dyes, organic charge generating materials such as indigo pigments, quinacridone pigments, or azo pigments.

Among the above charge generating materials used in the present invention, the azo pigments, in particular, cover various types, but typical structural examples of particularly highly effective azo pigments are shown below.

When, as the general formula of an azo pigment, the central skeleton is represented by A as shown below, and the coupler moiety, by Cp:

(wherein n is 2 or 3)

First, examples of A may include the following:

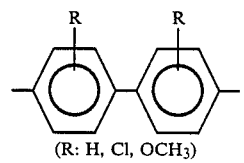

(R: H, Cl, OCH₃)

A-1

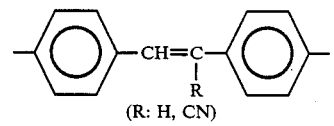

(R: H, CN)

A-2

-continued
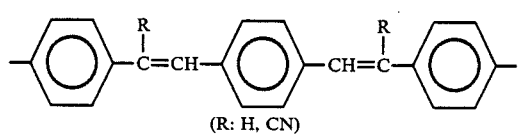   A-3
(R: H, CN)
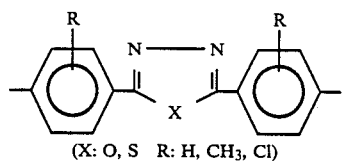   A-4
(X: O, S  R: H, CH₃, Cl)
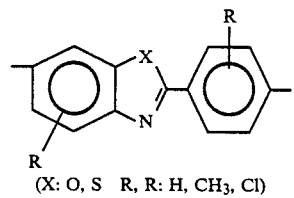   A-5
(X: O, S  R, R: H, CH₃, Cl)
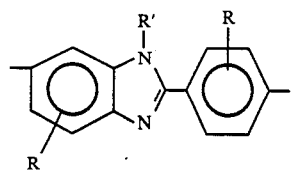   A-6
(R, R: H, CH₃, Cl, etc.  R': H, CH₃, )
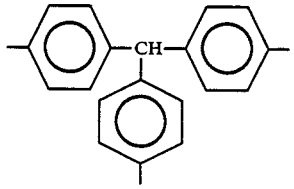   A-7
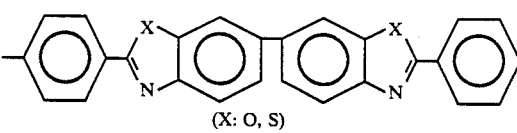   A-8
(X: O, S)
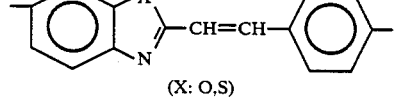   A-9
(X: O, S)
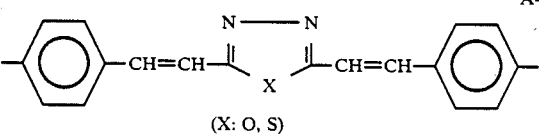   A-10
(X: O, S)
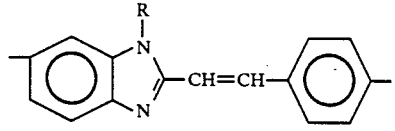   A-11
(R: H, CH₃)
-continued
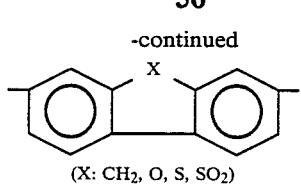   A-12
(X: CH₂, O, S, SO₂)
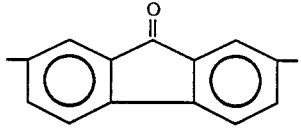   A-13
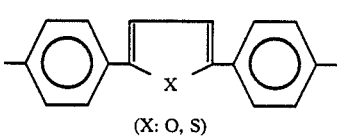   A-14
(X: O, S)
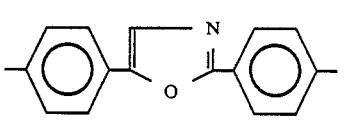   A-15
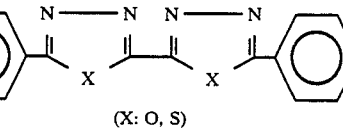   A-16
(X: O, S)
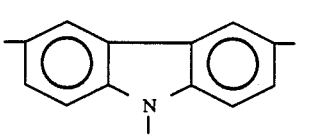   A-17
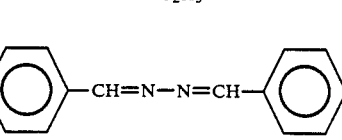   A-18
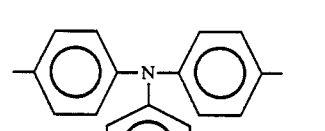   A-19
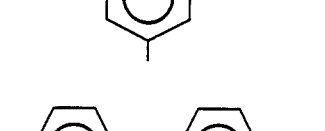   A-20
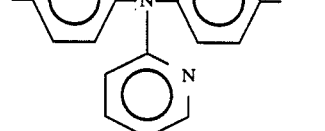   A-21
(R: H, CH₃)
Also, examples of Cp may include the following:

Cp-1
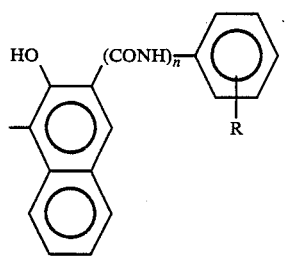

(R: H, halogen, alkoxy, alkyl, nitro, etc.
n: 1 or 2)

Cp-2
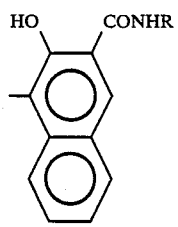

(R: CH₃, C₂H₅, C₃H₇)

Cp-3
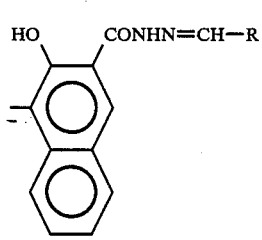

(R: alkyl, R': H, halogen, alkoxy, alkyl, nitro, etc.)

Cp-4
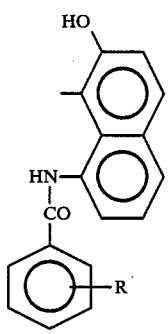

(R: H, halogen, alkoxy, alkyl, nitro, etc.)

Cp-5
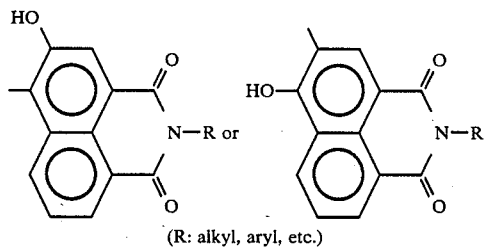

(R: alkyl, aryl, etc.)

Cp-6
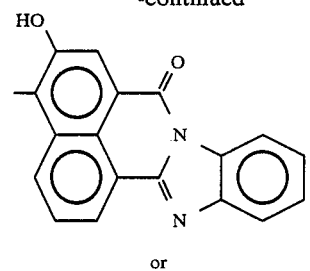

or

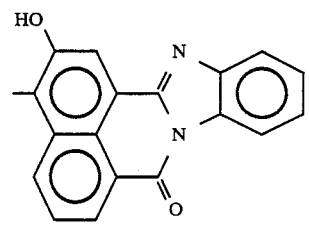

Cp-7
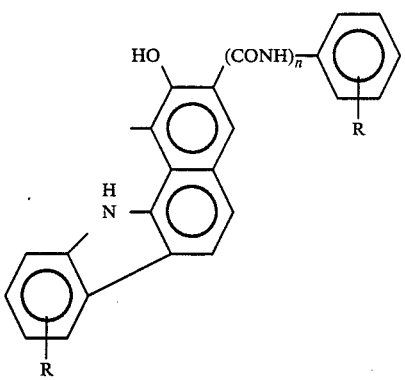

(R,R: H, halogen, alkoxy, alkyl, nitro, etc.
n: 1 or 2)

These central skeleton A and coupler Cp may be appropriately combined to form a pigment serving as the charge generating material.

The charge generation layer can be formed by dispersing the above charge generating material in a suitable binder and coating the resulting solution on a support, or can be obtained by forming a deposited film by using a vacuum deposition apparatus. The above binder can be selected from a vast range of insulating resins, and also can be selected from organic photoconductive polymers such as poly-N-vinyl carbazole, polyvinyl anthracene and polyvinyl pyrene. They may preferably include insulating resins such as polyvinyl butyral, polyarylates (e.g., a condensation polymer of bisphenol A with phthalic acid), polycarbonates, polyesters, phenoxy resins, polyvinyl acetate, acrylic resins, polyacrylamide resins, polyamides, polyvinyl pyridine, cellulose type resins, urethane resins, epoxy resins, casein, polyvinyl alcohol and polyvinyl pyrrolidone. The resin may suitably be contained in the charge generation layer in an amount of not more than 80% by weight, and preferably not more than 40% by weight. Usable as the organic solvent used in the coating are alcohols such as methanol, ethanol and isopropanol, ketones such as acetone, methyl ethyl ketone and cyclohexane, amides such as N,N-dimethylformamide, N,N-dimethylacetamide, sulfoxides such as dimethylsulfoxide, ethers such as tetraydrofuran, dioxane and ethylene glycol monomethyl ether, esters such as methyl acetate and ethyl acetate, aliphatic halogenated hydrocarbons such as chloroform, methylene chloride, dichloroethylene, carbon tetrachloride and trichloroethylene, or aromatics such as benzene, toluene, xylene, monochlorobenzene and dichlorobenzene.

The coating can be carried out by using coating methods previously described.

The charge generation layer may preferably contain the above organic photoconductive material as much as possible in order to obtain a sufficient absorbance, and at the same time comprise a thin film layer, for example, a thin film layer having a film thickness of not more than 5 µm, and preferably from 0.01µm to 1 µm, in order to inject carriers into the charge transport layer within the life of the charge carriers generated. This is because a greater part of the amount of incident light is absorbed in the charge generation layer to produce a large number of charge carriers, and moreover the charge carriers generated are required to be injected into the charge transport layer without deactivation by recombination or trapping.

The photosensitive layer composed of a laminated structure comprising such a charge generation layer and charge transport layer is provided on a conductive support. Usable as the conductive support are those which the support itself is conductive, as exemplified by those made of aluminum, aluminum alloys, stainless steel, nickel and indium. Besides these, there can be also used plastics (as exemplified by polyethylene, polypropylene, polyvinyl chloride, polyethylene terephthalate, acrylic resins and polyethylene fluoride) having a layer formed into a film by vacuum deposition of aluminum, aluminum alloys, indium oxide, tin oxide or the like, supports comprising plastics or the above conductive support covered thereon with conductive particles (as exemplified by aluminum powder, titanium oxide, tin oxide, zinc oxide, carbon black and silver particles) together with a suitable binder, supports comprising plastics or paper impregnated with the conductive particles, and supports comprising plastics having conductive polymers.

A subbing layer having a barrier function and an adhesion function may be provided between the conductive support and photosensitive layer. The subbing layer can be formed by casein, polyvinyl alcohol, nitrocellulose, an ethylene/acrylic acid copolymer, polyamides, polyurethanes, gelatin, aluminum oxide, etc.

The subbing layer may suitably have a film thickness of from 0.1 µm to 5 µm, and preferably from 0.5 µm to 3 µm.

In the case when the charge generation layer constitutes the uppermost layer, it is often practiced that the thickness thereof is made to be reasonably greater than that of a usual charge generation layer chiefly because of the problem of print resistance and that the charge transporting material is added thereto in order to increase the carrying performance of carriers. In this case also, the compound according to the present invention can be used as an additive for making stable the potential characteristics of the charge transporting material.

In another embodiment of the present invention, the above disazo pigments, or the pigments or dyes having a photoconductivity, such as pyrylium dyes, thiapyrylium dyes, selenapyrylium dyes, benzopyrylium dyes, benzothiapyrylium dyes, naphthopyrylium dyes and naphthothiapyrylium dyes, as disclosed in U.S. Pat. Nos. 3,554,745, No. 3,567,438, No. 3,586,500, etc. can be used also as sensitizers.

In still another embodiment, a eutectic complex of a pyrylium dye with an electrically insulating polymer having an alkylidene diarylene moiety, as disclosed in U.S. Pat. No. 3,684,502, etc., can also be used as a sensitizer. This eutectic complex can be obtained as a particulate eutectic complex by dissolving, for example, 4-[4-bis-(2-chloroethyl)aminophenyl]-2,6-diphenylthiapyrylium perchlorate and poly(4,4'-isopropylidene diphenylene carbonate) in a halogenated hydrocarbon solvent (as exemplified by dichloromethane, chloroform, carbon tetrachloride, 1,1-dichloroethane, 1,2-dichloroethane, 1,1,2-trichloroethane, chlorobenzene, bromobenzene or 1,2-dichlorobenzene), followed by addition thereto of a non-polar solvent (as exemplified by hexane, octane, decane, 2,2,4-trimethylbenzene or ligroin). The electrophotographic photosensitive member in this embodiment may contain a styrene/butadiene copolymer, a silicone resin, a vinyl resin, a vinylidene chloride/acylonitrile copolymer, a styrene/acrylonitrile copolymer, a vinyl acetate/vinyl chloride copolymer, polyvinyl butyral, polymethyl methacrylate, poly-N-butyl methacrylate, polyesters, cellulose esters, or the like as a binder.

The electrophotographic photosensitive member of the present invention is not only utilized in electrophotographic copying machines, but also can be widely used in the fields to which the electrophotography is applied, such as laser printers, CRT printers, and electrophotographic plate-making systems.

The present invention can give an electrophotographic photosensitive member that can have a high sensitivity and can suffer less potential fluctuation even when the charge and exposure to light are repeated over a long period of time.

The present invention will be described below by giving Examples.

Examples 1 to 4 & Comparative Example 1

A disazo pigment (5 g) represented by the following structural formula was dispersed for 24 hours by means of a sand mill together with a solution obtained by dissolving 2 g of a butyral resin (degree of butyralization: 70 mol %) in 100 ml of cyclohexanone, to prepare a coating solution.

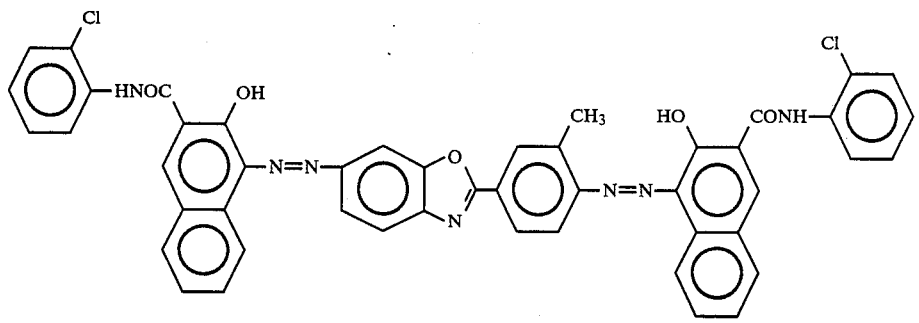

The resulting solution was coated on an aluminum sheet by Meyer bar coating so as to give a dried film thickness of 0.2 μm to form a charge generation layer.

Next, as a charge transporting material 10 g of a hydrazone compound of the following structural formula, 1.0 g of the above exemplary compound No. 1-4 and 10 g of a polycarbonate resin (average molecular weight: 20,000) were dissolved in 70 g of monochlorobenzene, and the resulting solution was coated on the charge generation layer by Meyer bar coating to provide a charge transport layer having a dried film thickness of 20 μm, thus preparing an electrophotographic photosensitive member having a photosensitive layer of a lamination type.

Canon K.K. and the copying of 50,000 sheets was carried out using the same machine, to measure the fluctuation of light portion potential ($V_L$) and dark portion potential ($V_D$) observed at the initial stage and after the 50,000 sheet copying.

The initial VD and VL were so set as to be $-700$ V and $-200$ V, respectively. Also, photosensitive members were prepared in the same manner as in Example 1 except that the exemplary compounds No. 2-2, No. 3-1 and No. 4-1 were each used in place of the above exemplary compound No. 1-4, to similarly carry out the measurement. For comparison, also prepared was a photosensitive member comprised of only a charge transporting material containing none of the exemplary compound No. 1-4, to similarly carry out the measurement.

Results obtained are shown in Table 1.

TABLE 1

| Example No. | Exemplary Comp. No. | $V_0$ (−V) | $V_1$ (−V) | $E_{\frac{1}{2}}$ (lux · sec) | Initial potential $V_D$(−V) | Initial potential $V_L$(−V) | Potential after 50,000 sheet duration $V_D$(−V) | Potential after 50,000 sheet duration $V_L$(−V) |
|---|---|---|---|---|---|---|---|---|
| 1 | 1-4 | 680 | 670 | 1.9 | 700 | 200 | 670 | 240 |
| 2 | 2-2 | 680 | 670 | 2.0 | 700 | 200 | 665 | 245 |
| 3 | 3-1 | 680 | 670 | 2.3 | 700 | 200 | 670 | 250 |
| 4 | 4-1 | 695 | 685 | 2.1 | 700 | 200 | 665 | 245 |
| Comparative Example 1: | | | | | | | | |
| 1 | — | 690 | 675 | 2.2 | 700 | 200 | 620 | 345 |

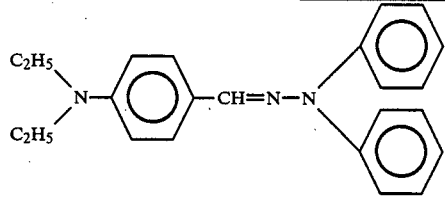

The electrophotographic photosensitive member thus prepared was subjected to corona charging at $-5$ kV according to a static method using an electrostatic copy paper tester, Model-SP-428 manufactured by Kawaguchi Denki K.K., which was retained in the dark for 1 second and then exposed to light at an illumination of 20 lux.

The amount of exposure ($E_{\frac{1}{2}}$) necessary for decaying to $\frac{1}{2}$ the surface potential ($V_0$) and the potential ($V_1$) after dark-decaying for 1 second was measured as the charging characteristics.

To further measure the fluctuation of light portion potential and dark portion potential after repeated use, the photosensitive member prepared in the present Example was stuck on a cylinder for a photosensitive drum of a PPC copying machine NP-3525 manufactured by Table 1 shows that employment of the compound of the present invention clearly results in retension of a good sensitivity and less fluctuation of the potential in the duration. Under the same conditions as for the initial stage, image reproduction was also carried out after the 50,000 sheet copying, resulting in little change in Examples but images with much ground fog in Comparative Example.

Examples 5 to 51 & Comparative Examples 2 to 21

Electrophotographic photosensitive members were prepared in the same manner as in Example 1 except that a compound of the following structural formula, having a ring of 7 members, was used in place of the charge transporting material used in the above Example 1;

pound No. 1-4 and a pigment having the following structural formula was used as a charge-generating material.

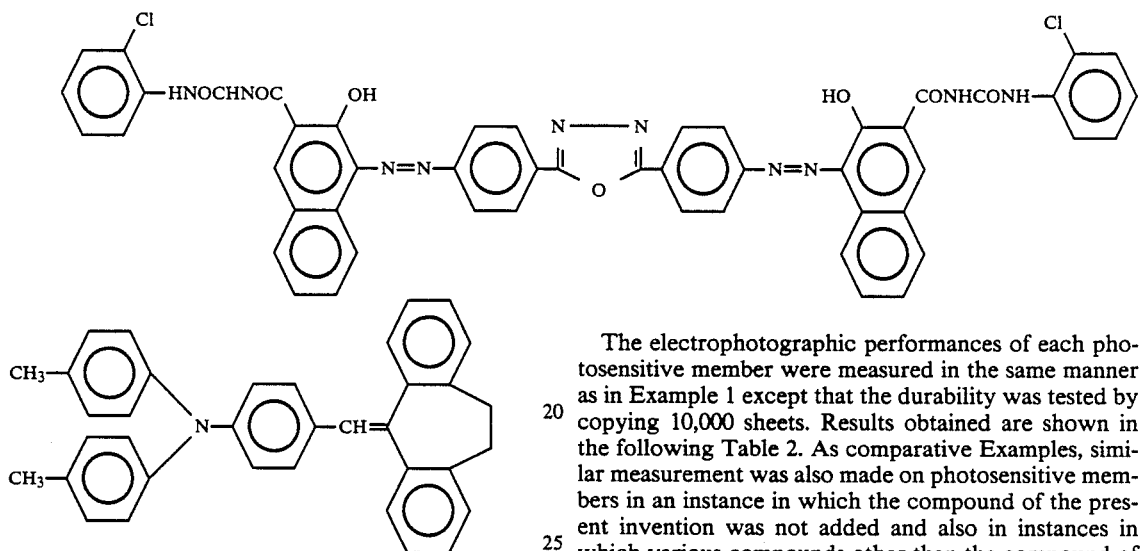

and further, the exemplary compounds as shown in Table 2 were added in place of the exemplary compound No. 1-4 and a pigment having the following structural formula was used as a charge-generating material.

The electrophotographic performances of each photosensitive member were measured in the same manner as in Example 1 except that the durability was tested by copying 10,000 sheets. Results obtained are shown in the following Table 2. As comparative Examples, similar measurement was also made on photosensitive members in an instance in which the compound of the present invention was not added and also in instances in which various compounds other than the compound of the present invention were added, to obtain the results shown in Table 3.

TABLE 2

| Example No. | Exemplary Comp. No. | $V_0$ (−V) | $V_1$ (−V) | $E_{\frac{1}{2}}$ (lux · sec) | Initial potential | | Potential after 10,000 sheet duration | |
|---|---|---|---|---|---|---|---|---|
| | | | | | $V_D(-V)$ | $V_L(-V)$ | $V_D(-V)$ | $V_L(-V)$ |
| 5 | 1-2 | 700 | 690 | 1.1 | 700 | 200 | 675 | 235 |
| 6 | 1-5 | 700 | 690 | 1.1 | 700 | 200 | 680 | 230 |
| 7 | 1-6 | 700 | 685 | 1.2 | 700 | 200 | 675 | 230 |
| 8 | 1-7 | 705 | 695 | 1.1 | 700 | 200 | 685 | 220 |
| 9 | 1-8 | 700 | 690 | 1.1 | 700 | 200 | 675 | 230 |
| 10 | 1-9 | 700 | 685 | 1.1 | 700 | 200 | 670 | 235 |
| 11 | 1-13 | 705 | 695 | 1.2 | 700 | 200 | 670 | 235 |
| 12 | 1-15 | 700 | 690 | 1.1 | 700 | 200 | 680 | 225 |
| 13 | 1-16 | 700 | 685 | 1.0 | 700 | 200 | 670 | 230 |
| 14 | 1-17 | 695 | 685 | 1.2 | 700 | 200 | 675 | 230 |
| 15 | 1-18 | 700 | 690 | 1.1 | 700 | 200 | 680 | 220 |
| 16 | 1-20 | 700 | 690 | 1.1 | 700 | 200 | 675 | 230 |
| 17 | 1-21 | 710 | 700 | 1.2 | 700 | 200 | 670 | 235 |
| 18 | 1-24 | 700 | 690 | 1.1 | 700 | 200 | 665 | 235 |
| 19 | 2-1 | 700 | 690 | 1.1 | 700 | 200 | 675 | 230 |
| 20 | 2-3 | 700 | 690 | 1.1 | 700 | 200 | 675 | 240 |
| 21 | 2-4 | 700 | 690 | 1.1 | 700 | 200 | 680 | 230 |
| 22 | 2-6 | 705 | 695 | 1.2 | 700 | 200 | 675 | 230 |
| 23 | 2-7 | 700 | 690 | 1.2 | 700 | 200 | 675 | 235 |
| 24 | 2-9 | 700 | 690 | 1.1 | 700 | 200 | 675 | 235 |
| 25 | 2-10 | 705 | 695 | 1.3 | 700 | 200 | 680 | 230 |
| 26 | 2-12 | 695 | 680 | 1.1 | 700 | 200 | 680 | 230 |
| 27 | 2-14 | 700 | 690 | 1.0 | 700 | 200 | 670 | 230 |
| 28 | 2-17 | 695 | 685 | 1.1 | 700 | 200 | 670 | 235 |
| 29 | 3-3 | 700 | 690 | 1.1 | 700 | 200 | 675 | 230 |
| 30 | 3-5 | 690 | 680 | 1.1 | 700 | 200 | 675 | 230 |
| 31 | 3-6 | 700 | 685 | 1.1 | 700 | 200 | 680 | 225 |
| 32 | 3-8 | 700 | 690 | 1.2 | 700 | 200 | 680 | 220 |
| 33 | 3-10 | 700 | 690 | 1.2 | 700 | 200 | 680 | 230 |
| 34 | 3-12 | 700 | 690 | 1.1 | 700 | 200 | 670 | 230 |
| 35 | 3-13 | 690 | 680 | 1.2 | 700 | 200 | 680 | 225 |
| 36 | 3-15 | 700 | 690 | 1.1 | 700 | 200 | 680 | 225 |
| 37 | 3-18 | 700 | 685 | 1.1 | 700 | 200 | 675 | 230 |
| 38 | 3-19 | 700 | 690 | 1.2 | 700 | 200 | 675 | 230 |
| 39 | 3-23 | 700 | 690 | 1.1 | 700 | 200 | 680 | 230 |
| 40 | 3-26 | 705 | 695 | 1.0 | 700 | 200 | 675 | 225 |
| 41 | 4-2 | 690 | 680 | 1.1 | 700 | 200 | 675 | 230 |
| 42 | 4-4 | 700 | 690 | 1.1 | 700 | 200 | 670 | 240 |
| 43 | 4-6 | 705 | 690 | 1.2 | 700 | 200 | 675 | 235 |
| 44 | 4-9 | 700 | 680 | 1.1 | 700 | 200 | 675 | 230 |
| 45 | 4-12 | 700 | 690 | 1.2 | 700 | 200 | 670 | 235 |
| 46 | 4-13 | 700 | 690 | 1.1 | 700 | 200 | 675 | 235 |

TABLE 2-continued

| Example No. | Exemplary Comp. No. | $V_0$ (−V) | $V_1$ (−V) | $E_{\frac{1}{2}}$ (lux · sec) | Initial potential $V_D$(−V) | $V_L$(−V) | Potential after 10,000 sheet duration $V_D$(−V) | $V_L$(−V) |
|---|---|---|---|---|---|---|---|---|
| 47 | 4-15 | 705 | 695 | 1.1 | 700 | 200 | 670 | 230 |
| 48 | 4-17 | 700 | 690 | 1.1 | 700 | 200 | 680 | 230 |
| 49 | 4-18 | 700 | 690 | 1.1 | 700 | 200 | 675 | 225 |
| 50 | 4-20 | 700 | 690 | 1.2 | 700 | 200 | 670 | 235 |
| 51 | 4-22 | 700 | 690 | 1.0 | 700 | 200 | 675 | 230 |

TABLE 3

| Comparative Example No. | Structural formula | $V_0$ (−V) | $V_1$ (−V) | $E_{\frac{1}{2}}$ (lux·sec) | Initial potential | | Potential after 10,000 sheet duration | |
|---|---|---|---|---|---|---|---|---|
| | | | | | $V_D$(−V) | $V_L$(−V) | $V_D$(−V) | $V_L$(−V) |
| 2 | No additive | 700 | 690 | 1.1 | 700 | 200 | 640 | 295 |
| 3 | (3,4-dimethoxyphenyl)diphenylamine | 700 | 690 | 1.1 | 700 | 200 | 630 | 305 |
| 4 | bis[4-(diphenylamino)phenyl]methyl ether | 705 | 690 | 1.2 | 700 | 200 | 620 | 330 |
| 5 | tris(4-methylthiophenyl)methane | 700 | 690 | 1.1 | 700 | 200 | 640 | 300 |
| 6 | 1-(4-methoxyphenyl)-2,2-bis(methylthio)ethylene | 700 | 690 | 1.3 | 700 | 200 | 630 | 305 |
| 7 | triazine derivative with SCH₃ groups | 705 | 690 | 1.1 | 700 | 200 | 645 | 300 |

TABLE 3-continued

| Comparative Example No. | Structural formula | $V_0$ (−V) | $V_1$ (−V) | $E_{\frac{1}{2}}$ (lux · sec) | Initial potential | | Potential after 10,000 sheet duration | |
|---|---|---|---|---|---|---|---|---|
| | | | | | $V_D$(−V) | $V_L$(−V) | $V_D$(−V) | $V_L$(−V) |
| 8 | NC,CN / O₂N-C₆H₄-C=C-C₆H₄-NO₂ | 700 | 690 | 1.3 | 700 | 200 | 635 | 315 |
| 9 | (C₆H₅)₂N-C₆H₄-OC₄H₉ (triphenylamine with OC₄H₉) | 700 | 690 | 1.1 | 700 | 200 | 625 | 310 |
| 10 | (C₆H₅)₂N-C₆H₄-O-C₆H₄-N(C₆H₅)₂ | 705 | 690 | 1.2 | 700 | 200 | 620 | 330 |
| 11 | C₆H₅NH-C₆H₄-CH₂-S-S-CH₂-C₆H₄-NHC₆H₅ | 700 | 690 | 1.2 | 700 | 200 | 600 | 335 |
| 12 | (C₆H₅S)₂CH-C₆H₄-CH₂NH-C₆H₅ | 700 | 690 | 1.1 | 700 | 200 | 630 | 305 |

TABLE 3-continued

| Comparative Example No. | Structural formula | $V_0$ (−V) | $V_1$ (−V) | $E_{\frac{1}{2}}$ (lux·sec) | Initial potential | | Potential after 10,000 sheet duration | |
|---|---|---|---|---|---|---|---|---|
| | | | | | $V_D$(−V) | $V_L$(−V) | $V_D$(−V) | $V_L$(−V) |
| 13 | [structure: bis(diphenylamino-phenylthio) compound] | 705 | 690 | 1.2 | 700 | 200 | 635 | 305 |
| 14 | [structure: triphenylmethane with phenylthio groups] | 700 | 690 | 1.3 | 700 | 200 | 635 | 315 |
| 15 | [structure: CH₂—CH=C(SPh)₂ with methoxyphenyl] | 700 | 690 | 1.2 | 700 | 200 | 625 | 310 |
| 16 | [structure: dimethoxyphenyl di(tolyl)amine] | 690 | 680 | 1.1 | 700 | 200 | 630 | 300 |

TABLE 3-continued

| Comparative Example No. | Structural formula | $V_0$ (−V) | $V_1$ (−V) | $E_{\frac{1}{2}}$ (lux·sec) | Initial potential | | Potential after 10,000 sheet duration | |
|---|---|---|---|---|---|---|---|---|
| | | | | | $V_D$(−V) | $V_L$(−V) | $V_D$(−V) | $V_L$(−V) |
| 17 | (structure) | 700 | 685 | 1.2 | 700 | 200 | 620 | 330 |
| 18 | (structure) | 700 | 685 | 1.3 | 700 | 200 | 620 | 335 |
| 19 | (structure) | 705 | 690 | 1.2 | 700 | 200 | 625 | 325 |
| 20 | (structure) | 700 | 685 | 1.2 | 700 | 200 | 635 | 290 |
| 21 | (structure) | 700 | 690 | 1.2 | 700 | 200 | 600 | 345 |

As is apparent from Table 2 and Table 3, better sensitivities are retained in the instances in which the compounds according to the present invention are used, than the instances in which the conventional ones are used.

Also, the above copying machine NP-3525 was used to carry out image reproduction, thereafter left to stand until next morning, and then a black paper was copied to obtain the result that all Examples in which the compound according to the present invention was contained in the photosensitive layer obtained good black images but Comparative Examples, though having differences in intensity, caused without exception the so-called brank area phenomenon that the part facing a charger comes off in white. This tells that the compound according to the present invention is very effective against ozone, $NO_x$, nitric acid, etc. generated in the copying machine, particularly in the charger.

Examples 52 to 85 & Comparative Example 22

Electrophotographic photosensitive members were prepared in the same manner as in Example 1 except that an azo pigment having the following structure was used as the charge generating material, the exemplary compounds as shown in Table 4 were used, and no additive was added.

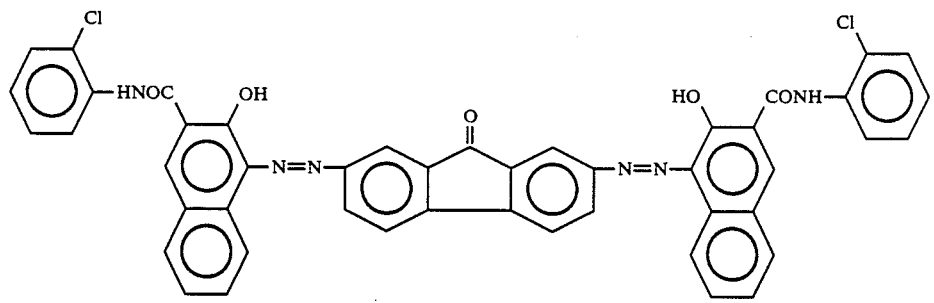

As Comparative Example, an electrophotographic photosensitive member was similarly prepared by using a compound of the following structure as the charge transporting material.

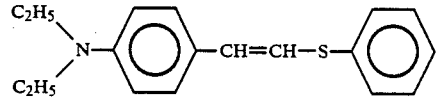

(A compound described in Japanese Patent Laid Open Application No. 62-134652)

This electrophotographic performances of each photosensitive member were measured in the same manner as in Example 5. Results obtained are shown in Table 4.

The compounds according to the present invention not only contribute the stability of potential but also exhibit superior characteristics in respect of sensitivity. On the other hand, the comparative example is not sufficiently contributory to the stability of potential, presumably because of the presence of one arylthio group.

TABLE 4

| Example No. | Exemplary Comp. No. | $V_0$ (−V) | $V_1$ (−V) | $E_{\frac{1}{2}}$ (lux · sec) | Initial potential $V_D$(−V) | Initial potential $V_L$(−V) | Potential after 10,000 sheet duration $V_D$(−V) | Potential after 10,000 sheet duration $V_L$(−V) |
|---|---|---|---|---|---|---|---|---|
| 52 | 1-25 | 700 | 685 | 2.0 | 700 | 200 | 675 | 230 |
| 53 | 1-27 | 690 | 680 | 2.6 | 700 | 200 | 675 | 225 |
| 54 | 1-28 | 700 | 690 | 2.9 | 700 | 200 | 680 | 230 |
| 55 | 1-30 | 705 | 695 | 3.0 | 700 | 200 | 675 | 235 |
| 56 | 1-34 | 700 | 690 | 3.3 | 700 | 200 | 680 | 230 |
| 57 | 1-36 | 700 | 685 | 2.1 | 700 | 200 | 675 | 230 |
| 58 | 1-37 | 695 | 685 | 2.1 | 700 | 200 | 680 | 225 |
| 59 | 1-39 | 695 | 680 | 2.0 | 700 | 200 | 675 | 230 |
| 60 | 1-40 | 700 | 690 | 2.1 | 700 | 200 | 680 | 230 |
| 61 | 1-41 | 700 | 690 | 2.3 | 700 | 200 | 675 | 235 |
| 62 | 1-42 | 695 | 685 | 2.7 | 700 | 200 | 680 | 230 |
| 63 | 2-13 | 700 | 680 | 2.7 | 700 | 200 | 675 | 235 |
| 64 | 2-14 | 690 | 675 | 2.6 | 700 | 200 | 670 | 230 |
| 65 | 2-16 | 700 | 690 | 2.9 | 700 | 200 | 675 | 240 |
| 66 | 2-18 | 700 | 690 | 2.1 | 700 | 200 | 675 | 230 |
| 67 | 2-20 | 700 | 690 | 2.3 | 700 | 200 | 670 | 240 |
| 68 | 3-25 | 695 | 680 | 2.7 | 700 | 200 | 675 | 235 |
| 69 | 3-26 | 700 | 685 | 2.4 | 700 | 200 | 675 | 230 |
| 70 | 3-28 | 700 | 690 | 2.6 | 700 | 200 | 680 | 230 |
| 71 | 3-30 | 700 | 690 | 2.6 | 700 | 200 | 675 | 235 |
| 72 | 3-31 | 700 | 685 | 2.9 | 700 | 200 | 670 | 240 |
| 73 | 3-32 | 700 | 685 | 2.2 | 700 | 200 | 675 | 225 |
| 74 | 3-33 | 690 | 680 | 2.5 | 700 | 200 | 680 | 225 |
| 75 | 3-35 | 700 | 685 | 1.9 | 700 | 200 | 675 | 230 |
| 76 | 3-36 | 700 | 690 | 1.8 | 700 | 200 | 685 | 225 |
| 77 | 3-39 | 690 | 670 | 2.3 | 700 | 200 | 670 | 235 |
| 78 | 3-41 | 700 | 690 | 2.7 | 700 | 200 | 670 | 235 |
| 79 | 4-24 | 700 | 685 | 2.5 | 700 | 200 | 670 | 230 |

TABLE 4-continued

| Exemplary Comp. No. | | $V_0$ (−V) | $V_1$ (−V) | $E_{\frac{1}{2}}$ (lux · sec) | Initial potential | | Potential after 10,000 sheet duration | |
|---|---|---|---|---|---|---|---|---|
| | | | | | $V_D$(−V) | $V_L$(−V) | $V_D$(−V) | $V_L$(−V) |
| 80 | 4–26 | 690 | 680 | 3.1 | 700 | 200 | 675 | 230 |
| 81 | 4–27 | 700 | 685 | 2.9 | 700 | 200 | 675 | 235 |
| 82 | 4–30 | 700 | 690 | 2.1 | 700 | 200 | 675 | 230 |
| 83 | 4–32 | 705 | 695 | 2.2 | 700 | 200 | 670 | 230 |
| 84 | 4–33 | 700 | 680 | 2.1 | 700 | 200 | 675 | 230 |
| 85 | 4–35 | 705 | 690 | 2.0 | 700 | 200 | 670 | 240 |
| Comparative Example 22: The compound set out above. | | 700 | 690 | 2.5 | 700 | 200 | 600 | 305 |

Example 86 & Comparative Examples 23, 24

A disazo pigment (5 g) represented by the following structural formula was dispersed for 24 hours by means of a sand mill together with a solution obtained by dissolving 2 g of a butyral resin (degree of butyralization: 70 mol %) in 100 ml of cyclohexanone, to prepare a coating solution.

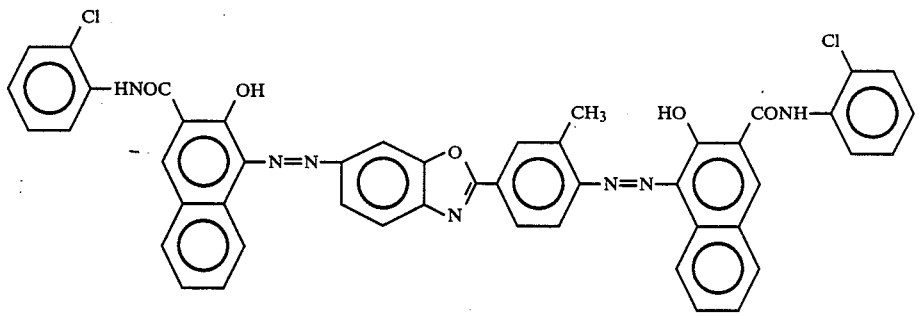

The resulting solution was coated on an aluminum sheet by Meyer bar coating so as to give a dried film thickness of 0.2 μm to form a charge generation layer.

Next, as a charge transporting material 10 g of the above exemplary compound No. 5–13, and 10 g of a polycarbonate resin (average molecular weight: 20,000) were dissolved in 70 g of monochlorobenzene, and the resulting solution was coated on the charge generation layer by Meyer bar coating to provide a charge transport layer having a dried film thickness of 20 μm, thus preparing an electrophotographic photosensitive member having a photosensitive layer of a lamination type.

The electrophotographic photosensitive member thus prepared was stuck on a cylinder for a photosensitive drum of a PPC copying machine NP-3525 manufactured by Canon Inc., used in Example 1, and the copying of 50,000 sheets was carried out using the same machine, to measure the fluctuation of light portion potential ($V_L$) and dark portion potential ($V_D$) observed at the initial stage, after 5,000 sheet copying and after 50,000 sheet copying.

The initial $V_D$ and $V_L$ were so set as to be −700 V and −200 V, respectively. For comparison, also prepared were similar photosensitive members but using as charge-transporting Compounds (A) and (B) represented by the following structural formulas, in place of the above exemplary compound, to similarly carry out the measurement.

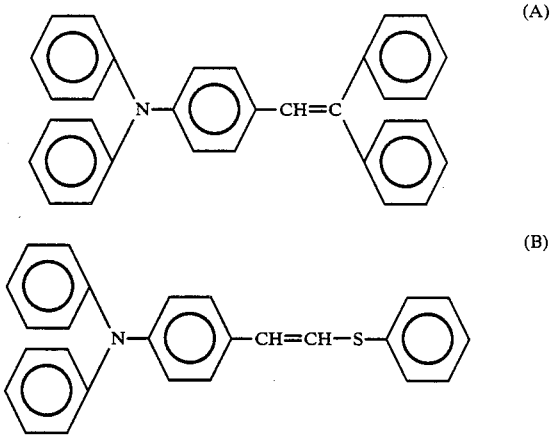

(Compounds described in Japanese Patent Laid Open Application No. 62-134652)

Results obtained are shown in Table 5.

TABLE 5

| Example No. | Exemplary Comp. No. | $V_0$ (−V) | $V_1$ (−V) | $E_{\frac{1}{2}}$ (lux · sec) | Initial potential (−V) | | Potential after duration of | |
|---|---|---|---|---|---|---|---|---|
| | | | | | | | 5,000 sheets (−V) | 50,000 sheets (−V) |
| 86 | 5–13 | 680 | 670 | 1.22 | $V_D$: | 700 | 690 | 670 |
| | | | | | $V_L$: | 200 | 210 | 235 |

TABLE 5-continued

| Example No. | Exemplary Comp. No. | $V_0$ (−V) | $V_1$ (−V) | $E_{\frac{1}{2}}$ (lux · sec) | Initial potential (−V) | | Potential after duration of 5,000 sheets (−V) | Potential after duration of 50,000 sheets (−V) |
|---|---|---|---|---|---|---|---|---|
| Comparative Example 23: The above compound (A) | | 690 | 680 | 1.35 | $V_D$: | 700 | 670 | 605 |
| | | | | | $V_L$: | 200 | 235 | 325 |
| Comparative Example 24: The above compound (B) | | 690 | 670 | 1.29 | $V_D$: | 700 | 675 | 625 |
| | | | | | $V_L$: | 200 | 225 | 305 |

As is apparent from Table 5, the photosensitive members having employed the compound of the present invention are seen to be stable photosensitive members having a high sensitivity and also having less fluctuation of potential even after the durability test of 50,000 sheets. In this connection, after the photosensitive members of Example 86 and Comparative Examples 23 and 24 were tested for the 50,000 sheet duration, image reproduction was carried out under the same conditions for the initial stage using the copying machine NP-3525 previously mentioned, to make examination. As a result, the ground fog was, though little seen in Example, considerable seriously seen in Comparative Examples.

Examples 87 to 100 & Comparative Examples 25 to 34

In these respective Examples, electrophotographic photosensitive members were prepared in the same manner as in Example 86 except that the exemplary compounds as shown in Table 6 were used as the charge transporting material in place of the exemplary compound No. 5-13 used in the above Example 86 and also an azo pigment having the following structure was used as the charge generating material.

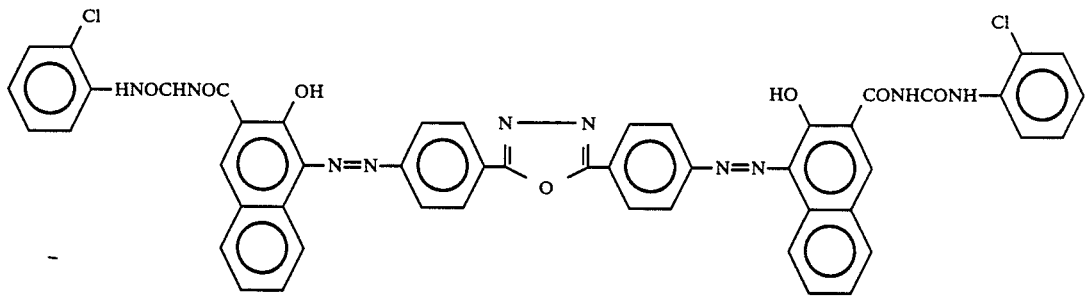

The electrophotographic characteristics of each photosensitive member were measured in the same manner as in Example 1. Results obtained are shown in Table 6. As comparative examples, similar measurement was also made on photosensitive members similarly prepared using several known compounds, and photosensitive members prepared by adding 10% by weight each of known stabilizers in the charge transporting material in Comparative Example 25. Results obtained are shown in Table 7.

TABLE 6

| Example No. | Exemplary Comp. No. | $V_0$ (−V) | $V_1$ (−V) | $E_{\frac{1}{2}}$ (lux · sec) | Initial potential $V_D$(−V) | Initial potential $V_L$(−V) | Potential after 50,000 sheet duration $V_D$(−V) | Potential after 50,000 sheet duration $V_L$(−V) |
|---|---|---|---|---|---|---|---|---|
| 87 | 5-1 | 690 | 670 | 1.8 | 700 | 200 | 660 | 245 |
| 88 | 5-4 | 695 | 680 | 1.3 | 700 | 200 | 670 | 235 |
| 89 | 5-5 | 700 | 690 | 1.7 | 700 | 200 | 665 | 235 |
| 90 | 5-8 | 700 | 690 | 2.1 | 700 | 200 | 665 | 245 |
| 91 | 5-11 | 690 | 675 | 2.0 | 700 | 200 | 670 | 240 |
| 92 | 5-16 | 685 | 670 | 2.3 | 700 | 200 | 675 | 230 |
| 93 | 5-18 | 705 | 695 | 3.6 | 700 | 200 | 665 | 245 |
| 94 | 5-21 | 700 | 690 | 1.4 | 700 | 200 | 660 | 240 |
| 95 | 5-25 | 695 | 680 | 1.3 | 700 | 200 | 665 | 240 |
| 96 | 5-28 | 685 | 670 | 1.6 | 700 | 200 | 660 | 245 |
| 97 | 5-29 | 700 | 690 | 2.0 | 700 | 200 | 665 | 235 |
| 98 | 5-34 | 695 | 685 | 3.6 | 700 | 200 | 660 | 240 |
| 99 | 5-35 | 695 | 680 | 2.8 | 700 | 200 | 655 | 235 |
| 100 | 5-38 | 700 | 690 | 1.8 | 700 | 200 | 665 | 245 |

TABLE 7

| Comparative Example No. | Charge-transporting material | Stabilizer | $V_0$ (−V) | $V_1$ (−V) | $E_{\frac{1}{2}}$ (lux·sec) | Initial potential (−V) | Potential after 50,000 sheet duration) (−V) |
|---|---|---|---|---|---|---|---|
| 25 | [structure] | None | 690 | 680 | 2.4 | $V_D$: 700<br>$V_L$: 200 | 640<br>335 |
| 26 | [structure] | None | 700 | 690 | 3.1 | $V_D$: 700<br>$V_L$: 200 | 600<br>350 |
| 27 | [structure] | None | 700 | 685 | 2.7 | $V_D$: 700<br>$V_L$: 200 | 605<br>295 |
| 28 | [structure] | None | 705 | 685 | 3.0 | $V_D$: 700<br>$V_L$: 200 | 630<br>315 |

TABLE 7-continued
| Comparative Example No. | Charge-transporting material | Stabilizer | $V_0$ (−V) | $V_1$ (−V) | $E_{\frac{1}{2}}$ (lux·sec) | Initial potential (−V) | Potential after 50,000 sheet duration) (−V) |
|---|---|---|---|---|---|---|---|
| 29 | 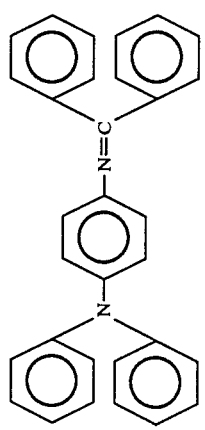 | None | 700 | 690 | 2.7 | $V_D$: 700<br>$V_L$: 200 | 610<br>330 |
| 30 | 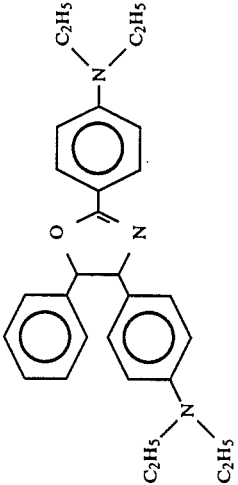 | None | 705 | 695 | 2.3 | $V_D$: 700<br>$V_L$: 200 | 630<br>320 |
| 31 | 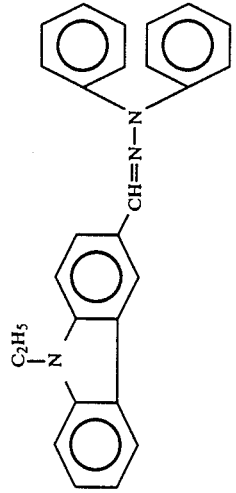 | 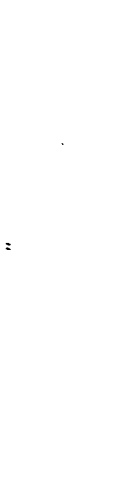 | 690 | 680 | 2.4 | $V_D$: 700<br>$V_L$: 200 | 650<br>315 |
| 32 | " |  | 695 | 680 | 2.5 | $V_D$: 700<br>$V_L$: 200 | 640<br>325 |

TABLE 7-continued
| Comparative Example No. | Charge-transporting material | Stabilizer | $V_0$ (−V) | $V_1$ (−V) | $E_{\frac{1}{2}}$ (lux·sec) | Initial potential (−V) | Potential after 50,000 sheet duration) (−V) |
|---|---|---|---|---|---|---|---|
| 33 | " | 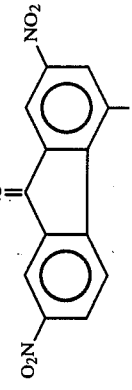 | 700 | 690 | 2.4 | $V_D$: 700<br>$V_L$: 200 | 620<br>330 |
| 34 | " | 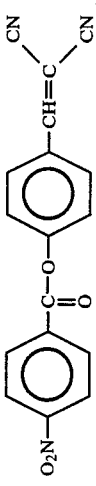 | 700 | 690 | 2.4 | $V_D$: 700<br>$V_L$: 200 | 650<br>315 |

(In this connection, $V_D$ was $-680$ V and $V_L$ was $-230$ in respect of Comparative Example in the 5,000 sheet duration, showing better effect than Comparative Example 25 in which no stabilizer was added and $V_D = -660$ $V_D$ and $V_L = -250$, but showing almost the same degree of fluctuation of potential after the 50,000 sheet duration.)

As is apparent from Table 6 and Table 7 set out above, the compound according to the present invention is seen to be able to give photosensitive members having a high sensitivity and also showing less fluctuation of potential in the 50,000 sheets duration.

It is further seen that, because of the greatness in the sensitivity and fluctuation of potential, particularly preferable results are obtained especially when in the present invention $Ar_2$ is a phenylene group and the thioether structures exist at two sites.

Example 101

An aqueous ammonia solution of casein (casein: 11.2 g; 28% ammonia water: 1 g; water: 222 mQ) was coated on an aluminum cylinder by blade coating to form a subbing layer having a dried film thickness of 1 μm.

Next, 10 g of a charge generating material represented by the following structural formula, 5 g of a butyral resin (butyralization degree: 63 mol %) and 200 g of cyclohexanone were dispersed for 48 hours using a ball mill dispersing machine.

The resulting dispersion was coated on the previously prepared subbing layer according to blade coating to form a charge generation layer having a dried film thickness of 0.15 μm.

Next, 10 g of the above exemplary compound No. 1-36 and 10 g of a polymethyl methacrylate resin (average molecular weight: 50,000) were dissolved in 70 g of monoclorobenzene, and the solution was coated by blade coating on the charge generation layer previously formed, to form a charge transport layer having a dried thickness of 19 μm, thus preparing a photosensitive member.

Photosensitive members were also prepared in the same manner but replacing the examplary compound No. 1-36 with the exemplary compounds as shown in Table 8.

Another photosensitive member was also prepared in the same manner but replacing the above charge generating material with the one having the following structural formula and also replacing the exemplary compound No. 1-36 with the exemplary compound No. 5-9.

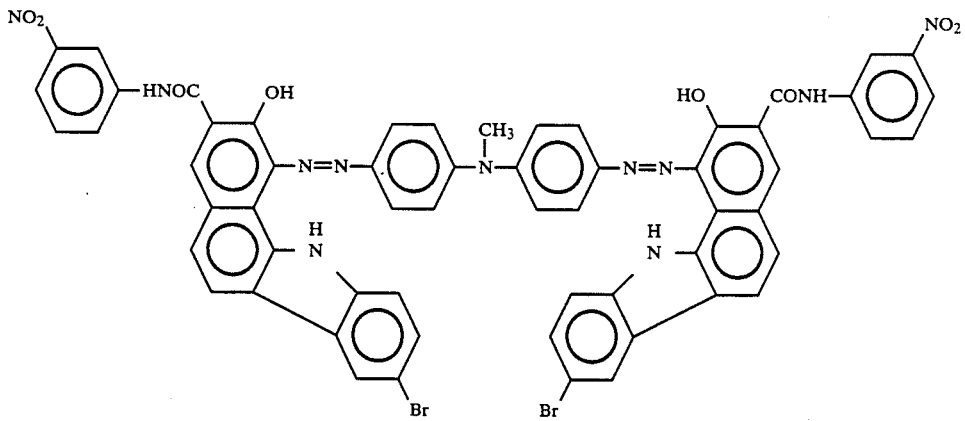

Corona charging at $-5$ kV was carried out on the photosensitive members thus prepared, to measure the surface potential produced at this time (initial potential $V_0$). Further measured were the surface potential after the photosensitive members were left to stand in the dark for 1 second. The sensitivity was evaluated by measuring the amount of exposure ($E_{\frac{1}{2}}$, microdule/cm²) necessary for decaying to 178 the potential $V_1$ after dark-decaying for 1 second. In this occasion, a gallium-/aluminum/arsenic three-component semiconductor

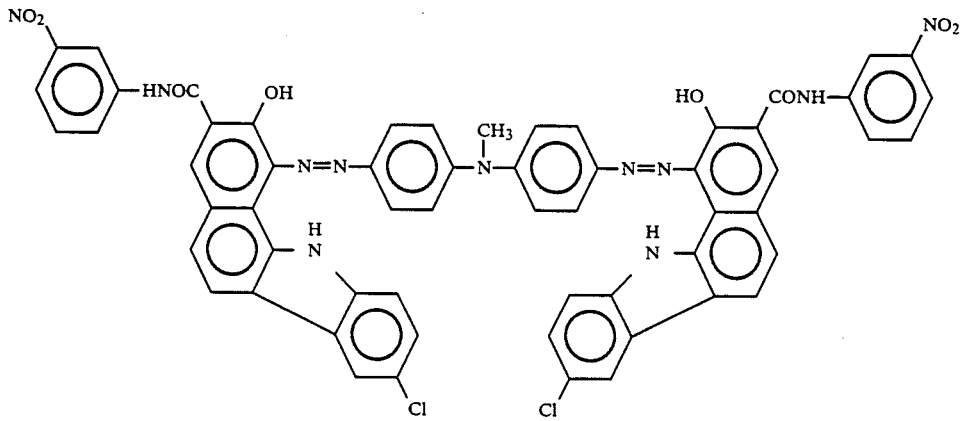

laser (output: 5 mW; oscillation wavelength: 780 nm) was used as a light source.

Results obtained are shown in Table 8.

TABLE 8

| Example No. | Exemplary Compound No. | $V_0$ (−V) | $V_1$ (−V) | $E_{\frac{1}{2}}$ (lux · sec) |
|---|---|---|---|---|
| 101 | 1-36 | 690 | 675 | 1.4 |
| 102 | 2-12 | 690 | 680 | 1.3 |
| 103 | 3-36 | 680 | 665 | 1.1 |
| 104 | 4-30 | 680 | 665 | 1.3 |
| 105 | 5-9 | 680 | 670 | 1.1 |

Next, the above photosensitive members were each set in a laser beam printer (LBP-CX, manufactured by Canon Inc.) which is a printer of a reversal development type electrophotographic system, equipped with the above semiconductor laser, to use test of actual image formation. Conditions were as follows: Surface potential after primary charging: −700 V; surface potential after imagewise exposure: −150 V (the amount of exposure: 2.0 μJ/cm$^2$); transfer potential: +700 V; polarity of developer: negative; processing speed: 50 mm/sec.; development condition (developing bias): −450 V; imagewise exposure scan system: image scanning; exposure to light before primary charging: red and whole-surface exposure of 50 lux.sec. Image formation was carried out by line-scanning the laser beam according to character signals and image signals, obtaining good prints in both characters and images. Image reproduction of 30,000 sheets was further carried out, obtaining stable and good prints from initial to 30,000 sheet printing.

Example 106

In 100 ml of a toluene (50 parts by weight)/dioxane (50 parts by weight) solution of a polyester (Polyester Adhesive 49000, available from Du Pont), 3 g of 4-(4-dimethylaminophenyl)-2,6-diphenylthiapyrylium perchlorate and 5 g of the above exemplary compound No. 5-15 were mixed, and the mixture was dispersed for 6 hours in a ball mill. The resulting dispersion was coated on an aluminum sheet by Meyer bar coating so as to give a film thickness of 18 μm after dried.

The electrophotographic characteristics of the photosensitive member thus prepared was measured in the same manner as in Example 1. Results obtained are shown below.

| | |
|---|---|
| $V_0$ | −680 V |
| $V_1$ | −670 V |
| $E_{\frac{1}{2}}$ | 1.4 lux · sec |
| Initial stage | |
| $V_D$ | −700 V |
| $V_L$ | −200 V |
| After 50,000 sheet durability test | |
| $V_D$ | −665 V |
| $V_L$ | −245 V |

Example 107

In 200 ml of dichloromethane, 3 g of 4-(4-diemthylaminophenyl)-2,6-diphenylthiapyrylium perchlorate and 3 g of poly(4,4'-isopropylidene diphenylene carbonate) were thoroughly dissolved, and thereafter 100 ml of toluene was added to precipitate a eutectic complex. The resulting precipitate was filtered, and thereafter dichloromethane was added to effect re-dissolution, followed by addition of 100 ml of n-hexane in the resulting solution to obtain a precipitate of an eutectic complex.

This eutectic complex (5 g) was added in 95 ml of a methanol solution containing 2 g of polyvinyl butyral. The resulting dispersion was coated on an aluminum sheet having a casein layer, by Meyer bar coating so as to give a film thickness of 0.4 μm after dried, to form a charge generation layer.

Subsequently, a charge transport layer was formed on this charge generation layer in the same manner as in Example 1 but using the exemplary compound No. 1-32, thus preparing a photosensitive member.

Also, photosensitive members were prepared in the same manner as in Example but replacing the exemplary compound No. 1-32 with the exemplary compounds as shown in Table 9.

The electrophotographic characteristics of the photosensitive members thus prepared were measured in the same manner as in Example 5. Results obtained are shown in Table 9.

TABLE 9

| Example No. | Exemplary Comp. No. | $V_0$ (−V) | $V_1$ (−V) | $E_{\frac{1}{2}}$ (lux · sec) | Initial potential | | Potential after 10,000 sheet duration | |
|---|---|---|---|---|---|---|---|---|
| | | | | | $V_D$(−V) | $V_L$(−V) | $V_D$(−V) | $V_L$(−V) |
| 107 | 1-32 | 690 | 675 | 1.7 | 700 | 200 | 665 | 235 |
| 108 | 2-19 | 690 | 675 | 1.6 | 700 | 200 | 675 | 230 |
| 109 | 3-29 | 690 | 675 | 1.3 | 700 | 200 | 675 | 230 |
| 110 | 4-3 | 690 | 675 | 1.2 | 700 | 200 | 670 | 230 |

Example 111

A photosensitive member was prepared in the same manner as in Example 107 except that the charge generation layer was formed to have a film thickness of 0.5 μm after dried and the exemplary compound No. 1-32 was replaced with the exemplary compound No. 5-23. The electrophotographic performances of this photosensitive member were measured in the same manner as in Example 1. Results obtained are shown below.

| | |
|---|---|
| $V_0$ | −700 V |
| $V_1$ | −690 V |
| $E_{\frac{1}{2}}$ | 1.9 lux · sec |
| Initial stage | |
| $V_D$ | −700 V |
| $V_L$ | −200 V |
| After 50,000 sheet durability test | |
| $V_D$ | −670 V |
| $V_L$ | −235 V |

We claim:

1. An electrophotographic photosensitive member comprising a photosensitive layer on a conductive support, wherein said photosensitive layer contains the following compound, said compound having structures (A) and (B) together in its structural formula:

(A) A disubstituted aminoaryl group represented by Formula (I):

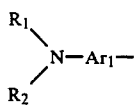   Formula (I)

wherein $R_1$ and $R_2$ each is an alkyl group, aryl group or aralkyl group that may have a substituent, or a residual group necessary to form a ring of 5 or 6 members by the combination of $R_1$ and $R_2$, and $Ar_1$ is an arylene group that may have a substituent;

(B) A (di) sulfide structure selected from the group consisting of (1) to (4):

(1) A chain sulfide structure represented by Formula (II):

Formula (II)

wherein $R_3$ is an alkyl group or aralkyl group that may have a substituent, (2) A chain disulfide structure represented by Formula (III):

Formula (III)

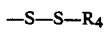

wherein $R_4$ is an alkyl group or aryl group or aralkyl group that may have a substituent, (3) A chain sulfide structure represented by Formula (IV) and a chain sulfide structure represented by:
Formula (V):
Formula (IV)

wherein $R_5$ is an aryl group that may have a substituent,
Formula (V)

wherein $R_6$ is an alkyl group, aryl group or aralkyl group that may have a substituent, (4) A cyclic sulfide structure or cyclic disulfide structure which is a 6- or 7-membered ring containing two or more sulfur atoms.

2. The electrophotographic photosensitive member according to claim 1, wherein said compound is used as a charge-transporting material.

3. The electrophotographic photosensitive member according to claim 1, wherein said compound is used as an additive to a charge-transporting material.

4. The electrophotographic photosensitive member according to claim 1, wherein the photosensitive layer has a laminated structure comprising a charge generation layer and a charge transport layer.

5. The electrophotographic photosensitive member according to claim 4, wherein the charge transport layer is laminated on the charge generation layer.

6. The electrophotographic photosensitive member according to claim 5, wherein the charge transport layer contains said compound as a charge-transporting material.

7. The electrophotographic photosensitive member according to claim 5, wherein the charge transport layer contains a charge-transporting material and said compound.

8. The electrophotographic photosensitive member according to claim 3 or 7, wherein the charge-transporting material comprises an organic photoconductive material.

9. The electrophotographic photosensitive member according to claim 1, wherein the photosensitive layer contains a charge generating material.

10. The electrophotographic photosensitive member according to claim 9, wherein the charge generating material comprises an azo pigment.

11. An electrophotographic photosensitive member comprising a photosensitive layer on a conductive support, wherein said photosensitive layer contains a thioether compound represented by Formula (VI):

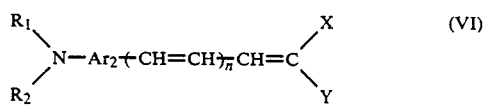

wherein $R_1$ and $R_2$ each is an alkyl group, aralkyl group or aryl group that may have a substituent, or a residual group necessary to form a ring of 5 to 6 members by the combination of $R_1$ with $R_2$; $Ar_2$ is an arylene group or divalent heterocylic group that may have a substituent; n is an integer of 0 of 1; X is $S-R_7$ or

Y is $S-R_9$, an alkyl group, aralkyl group or aryl group that may have a substituent, or X and Y is a residual group necessary to form a thioether ring by the combination of X with Y; and $R_7$, $R_8$ and $R_9$ each is an alkyl group, aralkyl group or aryl group that may have a substituent.

12. The electrophotographic photosensitive member according to claim 11, wherein Ar in Formula (VI) is a phenylene group.

13. The electrophotographic photosensitive member according to claim 11 or 12, wherein X and Y in Formula (VI) are both thioether structures represented by $S-R_3$.

14. The electrophotographic photosensitive member according to claim 13, wherein X and Y in Formula (VI) are both combined to form a thioether ring having two thioether structures.

15. The electrophotographic photosensitive member according to claim 11, wherein said compound is used as a charge-transporting material.

16. The electrophotographic photosensitive member according to claim 11, wherein the photosensitive layer has a laminated structure comprising a charge generation layer and a charge transport layer.

17. The electrophotographic photosensitive member according to claim 16, wherein the charge transport layer is laminated on the charge generation layer.

* * * * *

UNITED STATES PATENT AND TRADEMARK OFFICE
CERTIFICATE OF CORRECTION

PATENT NO. : 4,931,371
DATED : June 5, 1990
INVENTOR(S) : MASAKAZU MATSUMOTO, ET AL.          Page 1 of 6

It is certified that error appears in the above-identified patent and that said Letters Patent is hereby corrected as shown below:

ON THE TITLE PAGE

IN [56] REFERENCES CITED

U.S. PATENT DOCUMENTS, "Weidemann" should read --Wiedemann--.

FOREIGN PATENT DOCUMENTS, "53-26128  3/1978  Japan" should read --53-26128  7/1978  Japan-- and "62-134652  12/1985  Japan" should read --62-134652  6/1987  Japan--.

COLUMN 1

Line 46, "charge retension" should read --charge retention--.

COLUMN 3

Line 19, "or" (first occurrence) should read --of--.
Line 68, "naphtylmethyl" should read --naphthylmethyl--.

COLUMN 4

Line 39, "$5 \geq 0 + m + n \geq 1$" should read --$5 \geq 1 + m + n \geq 1$--.
Line 41, "$Q$ and m" should read --1 and m--.

COLUMN 5

Line 68, "trough" should read --through--.

UNITED STATES PATENT AND TRADEMARK OFFICE
CERTIFICATE OF CORRECTION

PATENT NO. : 4,931,371

DATED : June 5, 1990

INVENTOR(S) : MASAKAZU MATSUMOTO, ET AL.

It is certified that error appears in the above-identified patent and that said Letters Patent is hereby corrected as shown below:

COLUMN 6

Line 28, "$5 \geq 0 + m + n \geq 1$" should read
        --$5 \geq 1 + m + n \geq 1$--.

Line 30, "Q, m, n, k, and B" should read
        --1, m, n, k, and B--.

COLUMN 7

Line 23, "$5 \geq 0 + m + n \geq 2$" should read
        --$5 \geq 1 + m + n \geq 2$--.

Line 25, "Q, m, n, k, and B" should read
        --1, m, n, k, and B--.

COLUMN 8

Line 12, "molecule. Provided" should read
        --molecule, provided--.

Line 13, "result" should read --results--.

Line 43, "Q, m, p and q" should read --1, m, p and q--.

COLUMN 10

Line 12, "factors. Provided" should read
        --factors, provided--.

UNITED STATES PATENT AND TRADEMARK OFFICE
CERTIFICATE OF CORRECTION

PATENT NO. : 4,931,371
DATED : June 5, 1990
INVENTOR(S) : MASAKAZU MATSUMOTO, ET AL.

It is certified that error appears in the above-identified patent and that said Letters Patent is hereby corrected as shown below:

COLUMN 29

Example 3-39, " 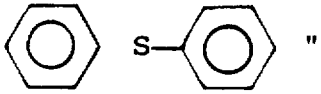 "

should read -- 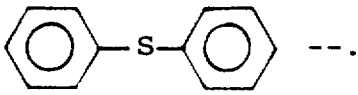 --.

COLUMN 52

Line 32, "dicyanometylenefluolenone," should read
--dicyanomethylenefluorenone,--.
Line 48, "3-metylbenzthiazoline-2-hydrazone," should read
--3-methylbenzthiazoline-2-hydrazone,--.

COLUMN 53

Line 9, "1,1-bis(4-N,N-dietylamino-2-methylphenyl)
heptane" should read --1,1-bis(4-N,N-
diethylamino-2-methylphenyl)heptane--.
Line 41, "material" should read --materials--.
Line 54, "may desirably" should read --may be
desirably--.

UNITED STATES PATENT AND TRADEMARK OFFICE
CERTIFICATE OF CORRECTION

PATENT NO. : 4,931,371

DATED : June 5, 1990

INVENTOR(S) : MASAKAZU MATSUMOTO, ET AL.

It is certified that error appears in the above-identified patent and that said Letters Patent is hereby corrected as shown below:

COLUMN 54

Line 8, "tolene," should read --toluene,--.
    Line 13, "be" should read --by--.
    Line 20, "additive" should read --additives--.
    Line 35, "azlenium" should read --azulenium--.

COLUMN 59

Line 2, "tetraydrofuran," should read --tetrahydrofuran,--.

COLUMN 60

Line 24, "bis-(2-chloroetyl)aminophenyl]-2,6-diphenyl-" should read --bis-(2-chloroethyl)aminophenyl]-2,6-diphenyl--.

COLUMN 62

Line 54, "retension" should read --retention--.

COLUMN 64

Line 21, "comparative Examples," should read --Comparative Examples,--.

COLUMN 75

Line 27, "brank area" should read --blank area--.

UNITED STATES PATENT AND TRADEMARK OFFICE
CERTIFICATE OF CORRECTION

PATENT NO. : 4,931,371
DATED : June 5, 1990
INVENTOR(S) : MASAKAZU MATSUMOTO, ET AL.

It is certified that error appears in the above-identified patent and that said Letters Patent is hereby corrected as shown below:

COLUMN 76

Line 29, "This" should read --The--.

COLUMN 79

Line 40, "siderable" should read --siderably-- and "seriously" should be deleted.

COLUMN 87

Line 5, "$V_D=-660\ V_D$" should read --$V_D=-660\ V$--.
    Line 40, "222 mQ" should read --222 ml--.

COLUMN 88

Line 47, "178" should read --1/2-- and delete boldface.

COLUMN 89

Line 18, "test" should read --tests--.
    Line 55, "after dried." should read --after being dried--.
    Line 57, "was" should read --were--.

UNITED STATES PATENT AND TRADEMARK OFFICE
CERTIFICATE OF CORRECTION

PATENT NO. : 4,931,371
DATED : June 5, 1990
INVENTOR(S) : MASAKAZU MATSUMOTO, ET AL.

It is certified that error appears in the above-identified patent and that said Letters Patent is hereby corrected as shown below:

COLUMN 90

Line 21, "after dried," should read --after being dried,--.
    Line 52, "after dried" should read --after being dried--.

COLUMN 91

Line 38, "by:" should read --by--.

Signed and Sealed this

Seventeenth Day of March, 1992

Attest:

HARRY F. MANBECK, JR.

*Attesting Officer*     *Commissioner of Patents and Trademarks*